(12) United States Patent
Armani et al.

(10) Patent No.: US 9,169,245 B2
(45) Date of Patent: Oct. 27, 2015

(54) INHIBITORS OF PDE4 ENZYME AND ANTAGONISTS OF MUSCARINIC M3 RECEPTOR

(71) Applicant: CHIESI FARMACEUTICI S.p.A., Parma (IT)

(72) Inventors: Elisabetta Armani, Parma (IT); Gabriele Amari, Parma (IT); Mauro Riccaboni, Parma (IT); Charles Baker-Glenn, Essex (GB)

(73) Assignee: Chiesi Farmaceutici S.p.A., Parma (IT)

( * ) Notice: Subject to any disclaimer, the term of this patent is extended or adjusted under 35 U.S.C. 154(b) by 22 days.

(21) Appl. No.: 14/097,397

(22) Filed: Dec. 5, 2013

(65) Prior Publication Data
US 2014/0155373 A1   Jun. 5, 2014

(30) Foreign Application Priority Data

Dec. 5, 2012  (EP) .................................. 12195726

(51) Int. Cl.
| | |
|---|---|
| C07D 453/02 | (2006.01) |
| C07D 453/00 | (2006.01) |
| C07D 401/14 | (2006.01) |
| C07D 401/12 | (2006.01) |
| C07D 417/14 | (2006.01) |
| C07D 417/12 | (2006.01) |
| A61K 31/444 | (2006.01) |
| A61K 31/4427 | (2006.01) |
| A61M 15/00 | (2006.01) |
| A61P 11/00 | (2006.01) |
| A61P 11/06 | (2006.01) |

(52) U.S. Cl.
CPC ............. *C07D 453/02* (2013.01); *C07D 401/12* (2013.01); *C07D 401/14* (2013.01); *C07D 417/12* (2013.01); *C07D 417/14* (2013.01); *C07D 453/00* (2013.01)

(58) Field of Classification Search
CPC .... C07F 453/00; C07F 453/02; C07F 401/14; C07F 401/12; C07F 417/14; C07F 417/12
USPC .................... 514/305, 210.18, 339, 340, 342; 546/133, 137, 269.7, 279.1, 347
See application file for complete search history.

(56) References Cited

U.S. PATENT DOCUMENTS

| | | |
|---|---|---|
| 7,820,698 B2 | 10/2010 | Rizzi et al. |
| 7,923,565 B2 | 4/2011 | Delcanale et al. |
| 7,968,724 B2 | 6/2011 | Armani et al. |
| 8,203,000 B2 | 6/2012 | Delcanale et al. |
| 8,383,826 B2 | 2/2013 | Delcanale et al. |
| 8,440,834 B2 | 5/2013 | Amari et al. |
| 8,648,204 B2 | 2/2014 | Amari et al. |
| 2011/0144075 A1 | 6/2011 | Delcanale et al. |
| 2013/0005716 A1 | 1/2013 | Armani et al. |
| 2013/0012487 A1 | 1/2013 | Amari et al. |
| 2013/0079313 A1 | 3/2013 | Armani et al. |
| 2013/0137648 A1 | 5/2013 | Delcanale et al. |
| 2013/0324501 A1 | 12/2013 | Armani et al. |

OTHER PUBLICATIONS

U.S. Appl. No. 14/560,140, filed Dec. 4, 2014, Amari, et al.
U.S. Appl. No. 14/560,009, filed Dec. 4, 2014, Amari, et al.
U.S. Appl. No. 14/097,693, filed Dec. 5, 2013, Armani, et al.
U.S. Appl. No. 14/097,586, filed Dec. 5, 2013, Armani, et al.
U.S. Appl. No. 14/097,445, filed Dec. 5, 2013, Armani, et al.
U.S. Appl. No. 14/048,651, filed Oct. 8, 2013, Armani, et al.
U.S. Appl. No. 14/164,527, filed Jan. 27, 2014, Armani, et al.

*Primary Examiner* — Sreeni Padmanabhan
*Assistant Examiner* — Irina Neagu
(74) *Attorney, Agent, or Firm* — Oblon, McClelland, Maier & Neustadt, L.L.P.

(57) ABSTRACT

Compounds of formula (I) described herein are both inhibitors of the phosphodiesterase 4 (PDE4) enzyme and muscarinic M3 receptor antagonists, and are useful for the prevention and/or treatment of diseases of the respiratory tract characterized by airway obstruction.

16 Claims, No Drawings

INHIBITORS OF PDE4 ENZYME AND ANTAGONISTS OF MUSCARINIC M3 RECEPTOR

CROSS REFERENCES TO RELATED APPLICATIONS

This application claims priority to European Patent Application No. 12195726.0 filed on Dec. 5, 2012, which is incorporated herein by reference in its entirety.

BACKGROUND OF THE INVENTION

1. Field of the Invention

The present invention relates to novel compounds which are both inhibitors of the phosphodiesterase 4 (PDE4) enzyme and muscarinic M3 receptor antagonists. The present invention also relates to methods of preparing such a compound, compositions which contain such a compound, and therapeutic uses of such a compound.

2. Discussion of the Background

Chronic obstructive pulmonary disease (COPD) is a respiratory disorder characterized by progressive, not fully reversible, airflow limitation associated with an abnormal pulmonary inflammatory response to noxious particles or gases. For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into 2 general classes: bronchodilators, (β2-adrenoceptor agonists, antimuscarinic agents and methylxanthines) and antiinflammatory agents (glucocorticosteroids and selective phosphodiesterase-4 (PDE4) inhibitors). Bronchodilator drugs are the current mainstay of treatment for symptoms relief.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients. Muscarinic antagonists block the effects of ACh at muscarinic receptors. Currently, there are five known muscarinic receptor subtypes (M1-M5); human airway smooth muscle contains M1, M2, and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells. These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention and constipation. Whereas dry mouth is the most common systemic anticholinergic side effect associated with the use of antimuscarinic antagonists as a result of the systemic blockade of M1 and M3 receptors the most potentially serious systemic effect is tachycardia, which results from the blockade of cardiac M2 receptors.

Inhaled anticholinergic antimuscarinic drugs approved for the treatment of COPD include ipratropium bromide (Atrovent®), oxitropium bromide (Oxivent®) and tiotropium bromide (Spiriva®). Both ipratropium and oxitropium are short-acting agents. In contrast, tiotropium bromide is the only long-acting antimuscarinic agent (LAMA) currently marketed for COPD, proved to be suitable for one-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure. Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over 4 weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 ml) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

SUMMARY OF THE INVENTION

Accordingly, it is one object of the present invention to provide novel compounds which act as inhibitors of the phosphodiesterase 4 (PDE4) enzyme and as muscarinic M3 receptor antagonists.

It is another object of the present invention to provide novel methods of preparing such a compound.

It is another object of the present invention to provide novel compositions which contain such a compound.

It is another object of the present invention to provide novel therapeutic uses of such a compound.

These and other objects, which will become apparent during the following detailed description, have been achieved by the inventors' discovery of compounds of formula (I):

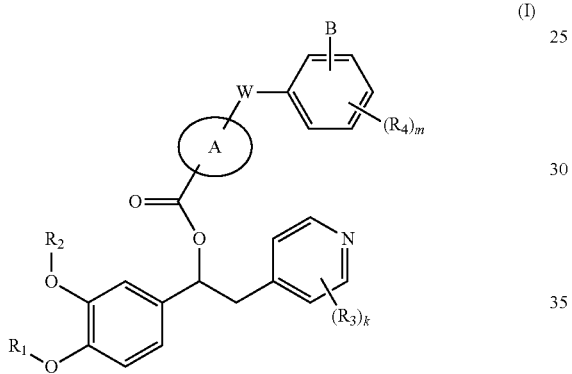

wherein:
$R_1$ and $R_2$ are different or the same and are independently selected from the group consisting of:
H;
$(C_3-C_7)$ cycloalkylcarbonyl;
$(C_1-C_6)$ alkyl, optionally substituted by one or more substituents selected from $(C_3-C_7)$ cycloalkyl and $(C_5-C_7)$ cycloalkenyl;
$(C_1-C_6)$ haloalkyl;
$(C_3-C_7)$ cycloalkyl;
$(C_5-C_7)$ cycloalkenyl;
$(C_2-C_6)$ alkenyl; and
$(C_2-C_6)$ alkynyl;
or $R_1$ and $R_2$, together with the interconnecting atoms, form a 2,2-difluoro-1,3-dioxolane ring of formula (r) fused to the phenyl moiety which bears groups —$OR_1$ and —$OR_2$, wherein asterisks indicate carbon atoms shared with such phenyl ring:

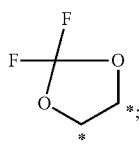

each $R_3$ is independently selected from the group consisting of CN, $NO_2$, $CF_3$ and a halogen atom;
k is zero or an integer ranging from 1 to 3;
A is a saturated and monocyclic $(C_3-C_7)$ heterocycloalkylene group;
W is selected from the group consisting of:
[1]-$(CH_2)_sC(O)$-[2] wherein s is zero or 1;
[1]-$C(O)(CH_2)_j$[2], wherein j is 1 or 2;
[1]-$SO_2(CH_2)_t$-[2] wherein t is zero, 1 or 2;
[1]-$(CH_2)_ySO_2$-[2] wherein y is 1 or 2;
[1]$(CH_2)_f$-[2] wherein f is 1 or 2; and
[1]$C(O)(CH_2)_2SO_2$-[2];
wherein [1] and [2] indicate the points of attachment for group W with, respectively, ring A and the phenyl moiety;
each R4 is independently hydrogen or is selected in the group consisting of halogen, $(C_1-C_4)$ alkyl, $(C_1-C_4)$ alkoxy, $(C_1-C_4)$haloalkyl, hydroxy, —$SO_2NR_5R_6$, —CN, and —$NR_7SO_2R_8$ and wherein $(C_1-C_4)$ alkyl and $(C_1-C_4)$ alkoxy are optionally substituted by one group $(C_3-C_7)$ cycloalkyl,
$R_5$ is hydrogen or $(C_1-C_6)$ alkyl;
$R_6$ is hydrogen or $(C_1-C_6)$ alkyl;
$R_7$ is hydrogen or $(C_1-C_6)$ alkyl;
$R_8$ is hydrogen or $(C_1-C_6)$ alkyl;
m is an integer ranging from 1 to 3;
B is selected from:
a group of formula (a) wherein the asterisk indicates the point of attachment for group B to the phenyl ring:

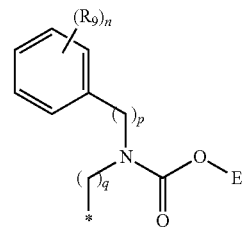

wherein
p is zero or 1;
q is zero or 1;
each $R_9$ is independently halogen, $(C_1-C_4)$ alkyl, $(C_1-C_4)$ alkoxy, $(C_{1-4})$haloalkyl, hydroxy, —$SO_2NR_{10}R_{11}$, —CN, or —$NR_{12}SO_2R_{13}$ and wherein said $(C_1-C_4)$ alkyl and said $(C_1-C_4)$ alkoxy are optionally substituted by one $(C_3-C_7)$ cycloalkyl group,
$R_{10}$ is hydrogen or $(C_1-C_6)$ alkyl;
$R_{11}$ is hydrogen or $(C_1-C_6)$ alkyl;
$R_{12}$ is hydrogen or $(C_1-C_6)$ alkyl;
$R_{13}$ is hydrogen or $(C_1-C_6)$ alkyl;
n is an integer ranging from 1 to 3;
E is a nitrogen containing group which is selected from
a group (c) which is —$(CH_2)_g$—$NR_{14}R_{15}$ wherein g is an integer ranging from 1 to 4 and $R_{14}$ and $R_{15}$ are independently hydrogen or $(C_1-C_4)$ alkyl; and
a group (d) which is a saturated monocyclic or bicyclic or tricyclic heterocyclic ring system optionally substituted by one or two groups $R_{16}$ which are at each occurrence independently $(C_1-C_4)$ alkyl or benzyl;

a group of formula (b) wherein the asterisk indicates the point of attachment for group B to the phenyl ring:

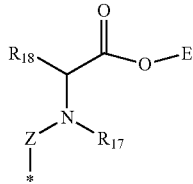

wherein
$R_{17}$ is selected from hydrogen, $(C_1-C_4)$ alkyl, and $-SO_2(C_1-C_4)$alkyl;
$R_{18}$ is selected from an aryl and a 5 to 11 membered heteroaryl, wherein such aryl or heteroaryl is optionally substituted by 1 to 3 groups $R_{19}$;
$R_{19}$ is at each occurrence independently halogen, $(C_1-C_4)$haloalkyl, hydroxy, $-SO_2NR_{20}R_{21}$, $-CN$, $-NR_{22}SO_2R_{23}$, $(C_1-C_4)$ alkyl, or $(C_1-C_4)$ alkoxy, wherein said $(C_1-C_4)$ alkyl and said $(C_1-C_4)$ alkoxy are optionally substituted by one $(C_3-C_7)$ cycloalkyl group, and wherein
$R_{20}$ is hydrogen or $(C_1-C_6)$ alkyl;
$R_{21}$ is hydrogen or $(C_1-C_6)$ alkyl;
$R_{22}$ is hydrogen or $(C_1-C_6)$ alkyl;
$R_{23}$ is hydrogen or $(C_1-C_6)$ alkyl;
Z is divalent radical selected from the group consisting of a bond, $-(CH_2)-$, $-(CH_2)_2-$, $-S-$, $-S(O)-$, $-S(O_2)-$, $-C(O)-$, and a group [5]-$(C_1-C_4)$alkylOC(O)-[6], wherein [5] and [6] represent, respectively the point of attachment of group Z to the phenyl ring and to the nitrogen atom; and
E is a group as above defined;
their N-oxides on the pyridine ring, and pharmaceutically acceptable salts, or solvates thereof.

The present invention further provides the corresponding N-oxides on the pyridine ring of compounds of formula (I).

The present invention also provides the pharmaceutically acceptable salts and/or solvates thereof.

The term "pharmaceutically acceptable salts", as used herein, refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

Those skilled in the art of organic chemistry will appreciate that many organic compounds can form complexes with solvents in which they are reacted or from which they are precipitated or crystallized. These complexes are known as "solvates." Pharmaceutically acceptable solvates of compound of the invention are within the scope of the present invention.

Included within the scope of the present invention are also polymorphs and crystalline forms of compounds of formula (I), of their N-oxides on the pyridine ring, or of pharmaceutically acceptable salts, or solvates thereof.

Hereinafter, compounds of formula (I), (IA), (IB), (IC), (Ia), (Ib), (Ic), (Id), and (I)', corresponding N-oxides on the pyridine ring, enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the invention."

The present invention further comprises a process for the preparation of compounds of the invention.

The present invention also provides pharmaceutical compositions of compounds of the invention either alone or in combination, in admixture with one or more pharmaceutically acceptable carriers.

In a further aspect the present invention provides the use of the compounds of the invention as a medicament.

In one aspect the present invention provides the use of the compounds of the invention for the manufacture of a medicament.

In particular, the present invention provides the use of the compounds of the invention for the prevention and/or treatment of any disease wherein an inhibition of PDE4 activity along with muscarinic M3 receptor antagonism is desirable.

In particular, the compounds of the present invention alone or combined with other active ingredients may be administered for the prevention and/or treatment of a disease the respiratory tract characterized by airway obstruction such as asthma and COPD. In one embodiment, the compounds of the invention may be administered for the prevention and/or treatment of COPD.

In a further aspect the present invention provides the use of compounds of the present invention for the preparation of a medicament for the prevention and/or treatment of any disease wherein an inhibition of PDE4 activity along with muscarinic M3 receptor antagonism is desirable.

Moreover the present invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the invention.

A further aspect of present the invention provides a suitable inhalation device, comprising a pharmaceutical composition of a compound of the invention, which may be respectively selected from a single- or multi-dose dry powder inhaler, a pressurized metered dosed inhaler or a nebulizer and in particular a soft mist nebulizer.

A further aspect of the present invention provides a kit comprising the pharmaceutical compositions of a compound of the invention either alone or in combination with one or more active ingredient and a device which may be a single- or multi-dose dry powder inhaler, a metered dose inhaler or a nebulizer.

DETAILED DESCRIPTION OF THE PREFERRED EMBODIMENTS

The term "halogen atoms" as used herein includes fluorine, chlorine, bromine, and iodine, preferably chlorine.

As used herein, the term "$(C_1-C_x)$ alkyl" where x is an integer greater than 1, refers to straight-chained and branched alkyl groups wherein the number of constituent carbon atoms is in the range 1 to x. Particular alkyl groups are methyl, ethyl, n-propyl, isopropyl, and t-butyl.

By analogy, the term "$(C_1-C_x)$alkylene", refers to a divalent $(C_1-C_x)$alkyl radical, wherein $(C_1-C_x)$alkyl is as above defined.

The term "$(C_1-C_x)$ alkoxyl" where x is an integer greater than 1, refers to straight-chained and branched alkoxy groups wherein the number of constituent carbon atoms is in the range 1 to x. Particular alkyl groups are methoxyl, ethoxyl, n-propoxyl, isopropoxyl, and t-ethoxyl.

The expressions "$(C_1-C_x)$haloalkyl" refer to the above defined "$(C_1-C_x)$alkyl" groups wherein one or more hydrogen atoms are replaced by one or more halogen atoms, which can be the same or different from each other. Examples of said $(C_1-C_6)$haloalkyl groups may thus include halogenated, polyhalogenated and fully halogenated alkyl groups wherein all of the hydrogen atoms are replaced by halogen atoms, e.g. trifluoromethyl or difluoro methyl groups.

The term "$(C_3-C_y)$ cycloalkyl" where y is an integer greater than or equal to 3 refers to saturated cyclic hydrocarbon groups containing from 3 to y ring carbon atoms. Examples include cyclopropyl, cyclobutyl, cyclopentyl, cyclohexyl, and cycloheptyl.

The derived expression "$(C_3-C_y)$heterocycloalkyl" refers to monocyclic $(C_3-C_y)$cycloalkyl groups, in which at least one ring carbon atom is replaced by a heteroatom (e.g. N, NH, S or O). Non-limiting examples of $(C_3-C_y)$ heterocycloalkyl are represented by pyrrolidinyl, thiazolidinyl, piperazinyl, piperidinyl, morpholinyl, thiomorpholinyl, and azetidinyl.

By analogy, the term "$(C_3-C_y)$heterocycloalkylene" refers to a divalent $(C_3-C_y)$heterocycloalkyl radical, wherein $(C_3-C_y)$ heterocycloalkyl is as above defined.

The expression "$(C_3-C_y)$cycloalkylcarbonyl" refers to $(C_3-C_y)$cycloalkylCO— groups wherein the group "$(C_3-C_y)$cycloalkyl" has the meaning above defined.

The term "$(C_2-C_6)$alkenyl" refers to straight or branched, conjugated or not conjugated, carbon chains with one or more double bonds, in cis or trans configuration, wherein the number atoms is in the range 2 to 6.

The term "$(C_5-C_z)$ cycloalkenyl" where z is an integer greater than or equal to 5 refers to cyclic hydrocarbon groups containing from 5 to z ring carbon atoms and one or more double bonds.

The term "$(C_2-C_6)$alkynyl" refers to straight or branched carbon chains with one or more triple bonds wherein the number atoms is in the range 2 to 6.

The term "aryl" refers to mono or bi-cyclic systems which have 6 to 10 ring atoms, wherein at least one ring is aromatic.

The expression "heteroaryl" refers to mono or bi-cyclic systems with 5 to 11 ring atoms, in which at least one ring is aromatic and in which at least one ring atom is a heteroatom (e.g. N, NH, S or O).

Non-limiting examples of suitable aryl or 5 and 6-membered heteroaryl monocyclic systems include, for instance, benzene (phenyl), thiophene (thiophenyl), pyrrole (pyrrolyl), pyrazole (pyrazolyl), imidazole (imidazolyl), triazole (triazolyl), tetrazole (tetrazolyl), isoxazole (isoxazolyl), oxazole (oxazolyl), isothiazole (isothiazolyl), thiazole (thiazolyl), pyridine (pyridinyl), furan (furanyl) derived radicals, and the like.

Non-limiting examples of suitable aryl or heteroaryl bicyclic systems include naphthalene (naphthyl), biphenylene (biphenylenyl), purine (purinyl), pteridine (pteridinyl), benzimidazole (benzimidazolyl), benzotriazole (benzotriazolyl), quinoline (quinolinyl), isoquinoline (isoquinolinyl), indole (indolyl), isoindole (isoindolyl), indazole (indazolyl), benzothiophene (benzothiophenyl), dihydrobenzo dioxin, dihydrobenzo dioxepin, benzo oxazin radicals, and the like.

As used herein, the expression "heterocyclic ring system" refers to optionally substituted mono-bi- or tri-cyclic ring systems which may be saturated, partially unsaturated or unsaturated, $(C_3-C_7)$ heterocycloalkyl or heteroaryl, having 5 to 11 ring atoms in which at least one ring atom is a heteroatom (e.g. N, S or O). Non-limiting examples of "heterocyclic ring system" are represented by: pyrrolidinyl, imidazolidinyl, piperazinyl, piperidinyl, quinuclidinyl, 8-azabicyclo[3.2.1] octanyl or dehydroxy scopine radicals all optionally substituted by $(C_1-C_4)$ alkyl or benzyl on a nitrogen atom.

The present invention is directed to a class of compounds which act both as inhibitors of the phosphodiesterase 4 (PDE4) enzyme and as muscarinic M3 receptor antagonists.

The present invention relates to derivatives of general formula (I), N-oxides on the pyridine ring and pharmaceutically acceptable salts or solvates thereof,

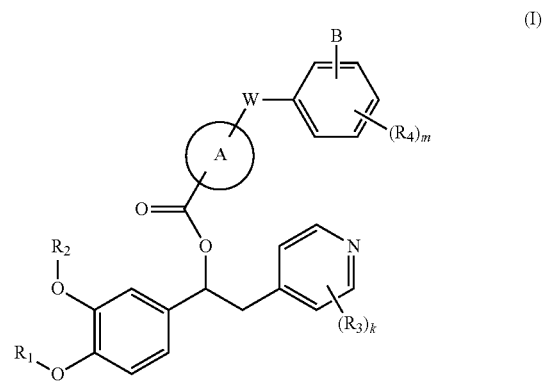

(I)

wherein $R_1$, $R_2$, $R_3$, $R_4$, A, W, B, m and k are as above defined.

It will be apparent to those skilled in the art that compounds of general formula (I) contain a stereogenic center, namely represented by the carbon atom (1) with an asterisk below, and therefore exist as optical stereoisomers.

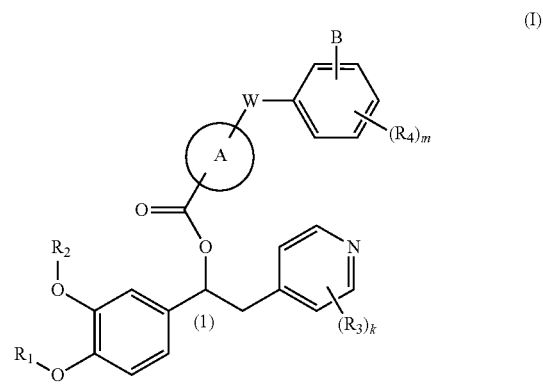

(I)

It will be apparent to the skilled person that compounds according to the invention may have at least two stereogenic centers, thus they may accordingly exist at least as four diastereoisomers. Where the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon (1) is that shown herebelow:

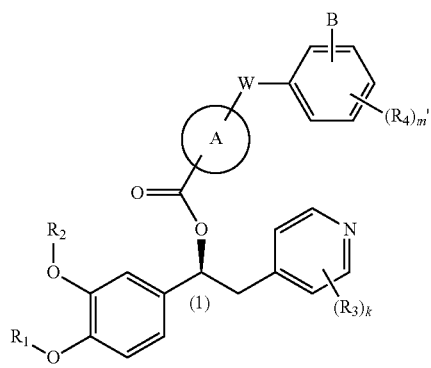

(I)

The absolute configuration for carbon (1) is assigned on the basis of Cahn-Ingold-Prelog nomenclature based on groups' priorities.

In one preferred embodiment, for compounds of formula (I), absolute configuration at carbon (1) is (S).

In one embodiment, when E is a group of formula (i) as below defined, compounds of formula (I) may exist as at least four diastereoisomers couples (Ia), (Ib), (Ic), and (Id), which are comprised within the scope of the present invention; each couple of diastereoisomers (Ia), (Ib), (Ic), and (Id) is constituted by a mixture of corresponding epimers at one stereogenic center identified.

It is to be understood that all preferred groups or embodiments described herebelow and hereabove for compounds of formula (I) may be combined among each other and apply to compounds of formula (IA), (IB), (Ia), (Ib), (Ic), (Id), and (I)' as well mutatis mutandis.

In one embodiment, the present invention provides compounds of formula (IA), which are N-oxides derivatives of the pyridine ring of compounds of formula (I), or pharmaceutically acceptable salts thereof:

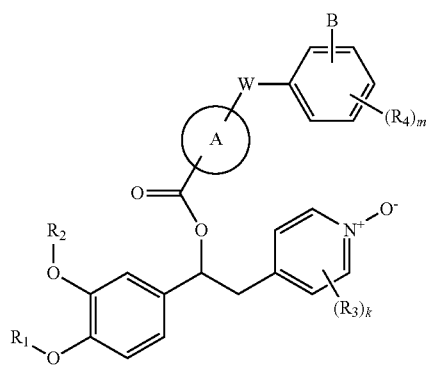

(IA)

wherein $R_1$, $R_2$, $R_3$, $R_4$, A, W, B, k and m are as defined above.

In one embodiment, the 4-pyridinyl ring has two $R_3$ substituents which are halogen atom. In a further preferred embodiment, such $R_3$ substituents are two chlorine atoms at positions 3 and 5 of the pyridine ring.

In one embodiment, $R_1$ is selected from $(C_1-C_6)$ haloalkyl and $(C_1-C_6)$ alkyl.

In one embodiment, $R_2$ is selected from $(C_3-C_7)$ cycloalkyl and $(C_1-C_6)$ alkyl optionally substituted by $(C_3-C_7)$ cycloalkyl.

In a further embodiment, $R_1$ is $(C_1-C_6)$ haloalkyl and $R_2$ is $(C_1-C_6)$ alkyl which is substituted by $(C_3-C_7)$ cycloalkyl.

In a still further embodiment, $R_1$ is $(C_1-C_6)$ alkyl and $R_2$ is $(C_1-C_6)$ alkyl.

In one embodiment, compounds of general formula (I) are provided wherein the 4-pyridinyl ring is substituted in 3 and 5 with two atoms of chlorine, according to the general formula (IB):

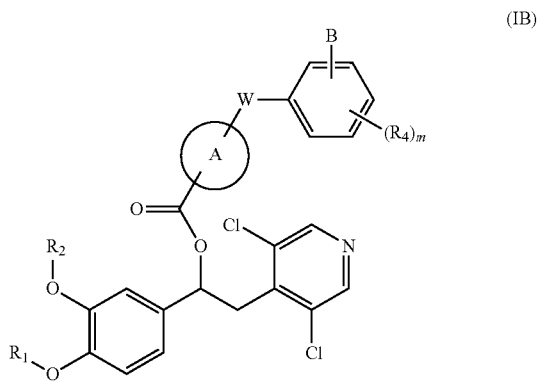

(IB)

wherein $R_1$, $R_2$, $R_4$, A, W, B and m are as defined above; and the corresponding N-oxide on the pyridine ring, or pharmaceutically acceptable salts and solvates thereof.

In one embodiment, A is a $(C_3-C_7)$ heterocycloalkylene group comprising a nitrogen atom which represents the connecting point to group W.

In another embodiment, A is selected in the list of di-radicals below reported:

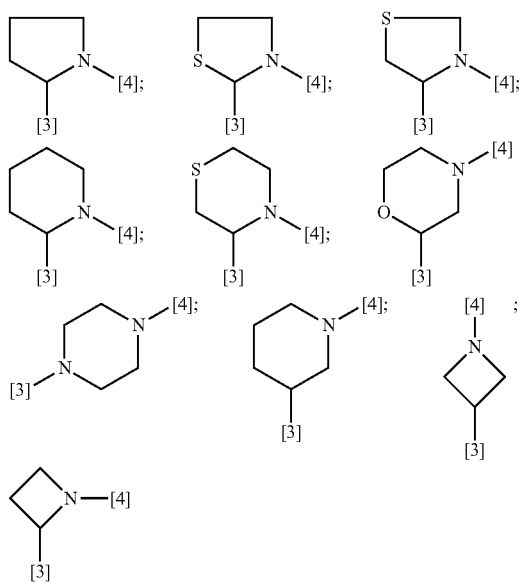

wherein the symbols [3] and [4] indicate the points of connection for group A with, respectively, the carbonyl group and W.

In one embodiment, E is a group (d) represented by a group of formula (i), (ii), (iii) or (iv):

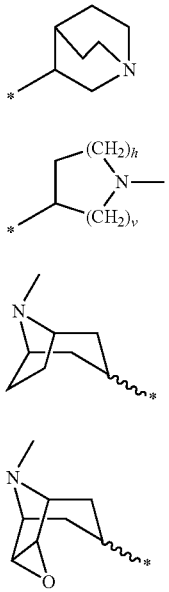

wherein
h=1, 2 or 3;
v=1, 2 or 3.

In another embodiment, E is a group (d) represented by a group of formula (i):

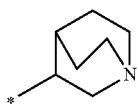

According to one embodiment, the present invention provides a compound selected from the group consisting of:
[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[2-oxo-1-phenyl-2-[(3R)-quinuclidin-3-yl]oxy-ethyl]carbamoyl]phenyl]sulfonylthiazolidine-2-carboxylate;
[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[(N-[(3R)-quinuclidin-3-yl]oxycarbonyl-anilino)methyl]benzoyl]thiazolidine-2-carboxylate;
[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[2-oxo-1-phenyl-2-[(3R)-quinuclidin-3-yl]oxy-ethyl]amino]phenyl]sulfonylpyrrolidine-2-carboxylate;
[(1S)-1-[3-(cyclopropylmethoxy)-4-(difluoromethoxy)phenyl]-2-(3,5-dichloro-1-oxido-pyridin-1-ium-4-yl)ethyl](2R)-1-[3-[[1-(3-fluorophenyl)-2-oxo-2-[(3R)-quinuclidin-3-yl]oxy-ethyl]amino]phenyl]sulfonylpyrrolidine-2-carboxylate;
[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[2-oxo-1-phenyl-2-[(3R)-quinuclidin-3-yl]oxy-ethyl]amino]phenyl]sulfonylthiazolidine-2-carboxylate;
[(1S)-2-(3,5-dichloro-1-oxido-pyridin-1-ium-4-yl)-1-(3,4-dimethoxyphenyl) ethyl](2S)-3-[3-[[2-oxo-1-phenyl-2-[(3R)-quinuclidin-3-yl]oxy-ethyl]carbamoyl]phenyl]sulfonylthiazolidine-2-carboxylate;
[(1S)-2-(3,5-dichloro-1-oxido-pyridin-1-ium-4-yl)-1-(3,4-dimethoxyphenyl)ethyl](2S)-1-[3-[(2-fluoro-N-[(3R)-quinuclidin-3-yl]oxycarbonyl-anilino)methyl]benzoyl]piperidine-2-carboxylate;
[(1S)-2-(3,5-dichloro-1-oxido-pyridin-1-ium-4-yl)-1-(3,4-dimethoxyphenyl)ethyl](4R)-3-[3-[(2-fluoro-N-[(3R)-quinuclidin-3-yl]oxycarbonyl-anilino)methyl]benzoyl]thiazolidine-4-carboxylate;
[(1S)-2-(3,5-dichloro-1-oxido-pyridin-1-ium-4-yl)-1-(3,4-dimethoxyphenyl)ethyl](2S)-1-[3-[(2-fluoro-N-[(3R)-quinuclidin-3-yl]oxycarbonyl-anilino)methyl]benzoyl]pyrrolidine-2-carboxylate;
[(1S)-2-(3,5-dichloro-1-oxido-pyridin-1-ium-4-yl)-1-(3,4-dimethoxyphenyl)ethyl]1-[3-[(2-fluoro-N-[(3R)-quinuclidin-3-yl]oxycarbonyl-anilino)methyl]benzoyl]azetidine-3-carboxylate;
[(1S)-2-(3,5-dichloro-1-oxido-pyridin-1-ium-4-yl)-1-(3,4-dimethoxyphenyl)ethyl](2S)-1-[4-[(2-fluoro-N-[(3R)-quinuclidin-3-yl]oxycarbonyl-anilino)methyl]phenyl]sulfonylpyrrolidine-2-carboxylate;
and pharmaceutically acceptable salts or solvates thereof.

Compounds of the invention may be prepared according to appropriate adaptation of synthetic approaches hereinbelow described in the Examples, in particular Examples 1, 3, 7, and 8.

Processes which can be used and which are described below should not be viewed as limiting the scope of the synthetic methods available for the preparation of the compounds of the invention.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form. In particular, functional groups present in the compounds of the invention or intermediates thereof which could generate unwanted side reaction and by-products, need to be properly protected before the alkylation, acylation, coupling, oxidation or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxy, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1999) which is incorporated herein by reference in its entirety).

Likewise, selective protection and deprotection of any of the said groups, for instance including carbonyl, hydroxyl, or amino groups, may be accomplished according to very well-known methods commonly employed in organic synthetic chemistry.

The N-oxides on the 4-pyridinyl ring of the compounds of general formula (I) and embodiments thereof may be prepared according to methods available in the literature and well known to the skilled person. For instance they may be prepared by dissolving the compound of general formula (I) or embodiments thereof in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid and peracetic acid.

Alternatively, in particular for those compounds comprising functional groups sensitive to oxidation, the corresponding N-oxides are prepared by carrying out the oxidation step before further functional groups are introduced.

In a preferred embodiment, the process for preparation of compounds of formula (I) or embodiments thereof is performed starting from N-oxide on the pyridine ring of intermediate compounds, thus allowing the preparation of compound of formula (I) or embodiments thereof in the form of N-oxides on the pyridine ring.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The present invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention or may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the present invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation. Inhalable preparations include inhalable powders, propellant-containing metered aerosols or propellant-free inhalable formulations and may be administered through a suitable inhalation device which may be respectively selected from dry powder inhaler, pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), and mucus regulators.

The present invention also provides combinations of a compound of the invention, with a β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol, and ASF-1020 and salts thereof.

The present invention also provides combinations of a compound of the invention, with a corticosteroid selected from the group consisting of fluticasone propionate, fluticasone furoate, mometasone furoate, beclometasone dipropionate, ciclesonide, budesonide, GSK 685698, and GSK 870086.

The present invention also provides combinations of a compound of the invention, with an antimuscarinic agent selected from the group consisting of aclidinium, umeclidinium, tiotropium, ipratropium, trospium, glycopyrronium and oxitropium salts.

The present invention also provides combinations of a compound of the invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the invention, with a P38 MAP kinase inhibitor selected from the group consisting of semapimod, talmapimod, pirfenidone, PH-797804, GSK-725, minokine, and losmapimod and salts thereof.

In a preferred embodiment, the present invention provides combinations of a compound of the invention with an IKK2 inhibitor.

The invention also provides combinations of a compound of the invention with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The invention also provides combinations of a compound of the invention with a leukotriene modulator selected from the group consisting of montelukast, zafirlukast, and pranlukast.

The invention also provides combinations of a compound of the invention with a NSAID selected from the group consisting of ibuprofen and ketoprofen.

The invention also provides combinations of a compound of the invention with a mucus regulator selected from the group consisting of INS-37217, diquafosol, sibenadet, CS-003, talnetant, DNK-333, MSI-1956, and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage comprised between 0.001 and 1000 mg/day, preferably between 0.1 and 500 mg/day.

When they are administered by inhalation route, the dosage of the compounds of the invention is advantageously comprised between 0.01 and 20 mg/day, preferably between 0.1 and 10 mg/day.

Preferably, the compounds of the invention alone or combined with other active ingredients may be administered for the prevention and/or treatment of any obstructive respiratory disease such as asthma, chronic bronchitis and chronic obstructive pulmonary disease (COPD).

However the compounds of the invention may be administered for the prevention and/or treatment of any disease wherein PDE4 inhibition or M3 antagonism is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Behçet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

General Experimental Details

NMR Characterization:

$^1$H-NMR spectra were recorded on a 400 MHz Varian AS400 spectrometer. Chemical shift are reported as δ values in ppm relative to trimethyl silane (TMS) as an internal standard. Coupling constants (J values) are given in hertz (Hz) and multiplicities are reported using the following abbreviation (s=singlet, d=doublet, =triplet, q=quartet, m=multiplet, br=broad, nd=not determined).

LC/UV/MS Analytical Methods:

LC/MS retention times are estimated to be affected by an experimental error of ±0.5 min.

LC/UV/MS—Method

LC instrument: Acquity Waters UPLC (or equivalent)

Column: Kinetex 1.7u XB-C18 100A 100×2.1 mm (Phenomenex)

Column Temperature (° C.) 50.0

Mobile phases: $HCOONH_4$ 0.025M pH3 (A); Acetonitrile+ 0.1% Formic Acid (B)

Flow (ml/min) 0.65 (split in MS 1:3)

Stop Time (mins) 10.0

Gradient:

| Time (min) | % A | % B |
| --- | --- | --- |
| 0.00 | 80.0 | 20.0 |
| 5.50 | 20.0 | 80.0 |
| 7.50 | 20.0 | 80.0 |
| 8.00 | 80.0 | 20.0 |
| 10.00 | 80.0 | 20.0 |

UV detection: wavelength 254 nm

Injection Volume (ul)—2.00

Sample solvents: Acetonitrile

MS instrument:

Method 1:

Waters ZQ (or equivalent)

Polarity ES+

Capillary (kV) 3.00

Cone (V) 20.00

Extractor (V) 3.00
RF Lens (V) 1.0
Polarity ES−
Capillary (kV) 3.00
Cone (V) 20.00
Extractor (V) 3.00
RF Lens (V) 1.0
Source Temperature (° C.) 110
Desolvation Temperature (° C.) 210
Cone Gas Flow (L/Hr) 150
Desolvation Gas Flow (L/Hr) 650
Mass range: 100 to 950
Scan time (sec): 0.32
Method 2:

LC-MS was performed on a Waters 2795 Alliance HT HPLC with Waters 2996 Diode Array Detector coupled to a Micromass ZQ, single quadrapole mass spectrometer using a Phenomenex Luna C18 (2) column (5 μm, 100×4.6 mm plus guard cartridge) with a linear gradient of 5-95% acetonitrile/water (with 0.1% formic acid in each mobile phase) within 3.5 minutes and held at 95% for 2.0 minutes.

Method 3:

LC-MS was performed on a Waters 2795 Alliance HT HPLC with Waters 2996 Diode Array Detector coupled to a Micromass ZQ, single quadrapole mass spectrometer using a Waters Xterra MS C18 column (5 μm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.

Preparative reverse-phase HPLC conditions:
Preparative HPLC—Method 1:
Waters Micromass ZQ/Sample manager 2767
Photodiode array detector 2996;
Column: XTerra Prep MS C18 Column (5 μm, 19×150 mm, Waters)
Flow rate: 20 ml/min with MS detection
UV wavelength: 254 nm.
Mobile phase: Solvent A (water:MeCN:HCOOH 95:5:0.05); Solvent B (water:MeCN:HCOOH 5:95:0.05)
Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

Example 1

Synthesis of [(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[2-oxo-1-phenyl-2-[(3R)-quinuclidin-3-yl]oxy-ethyl]carbamoyl]phenyl]sulfonylthiazolidine-2-carboxylate (E1)

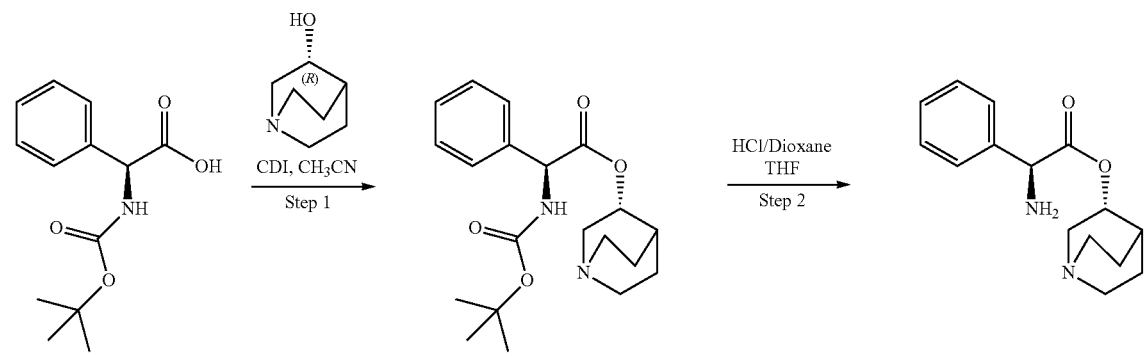

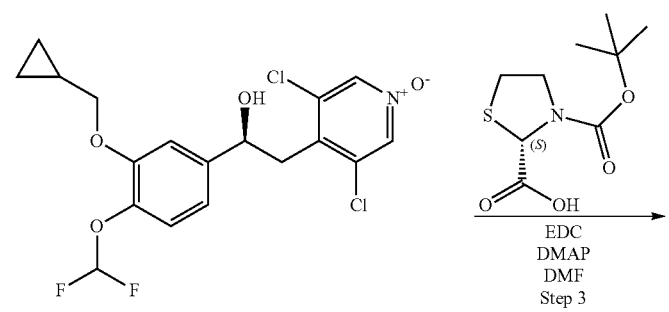

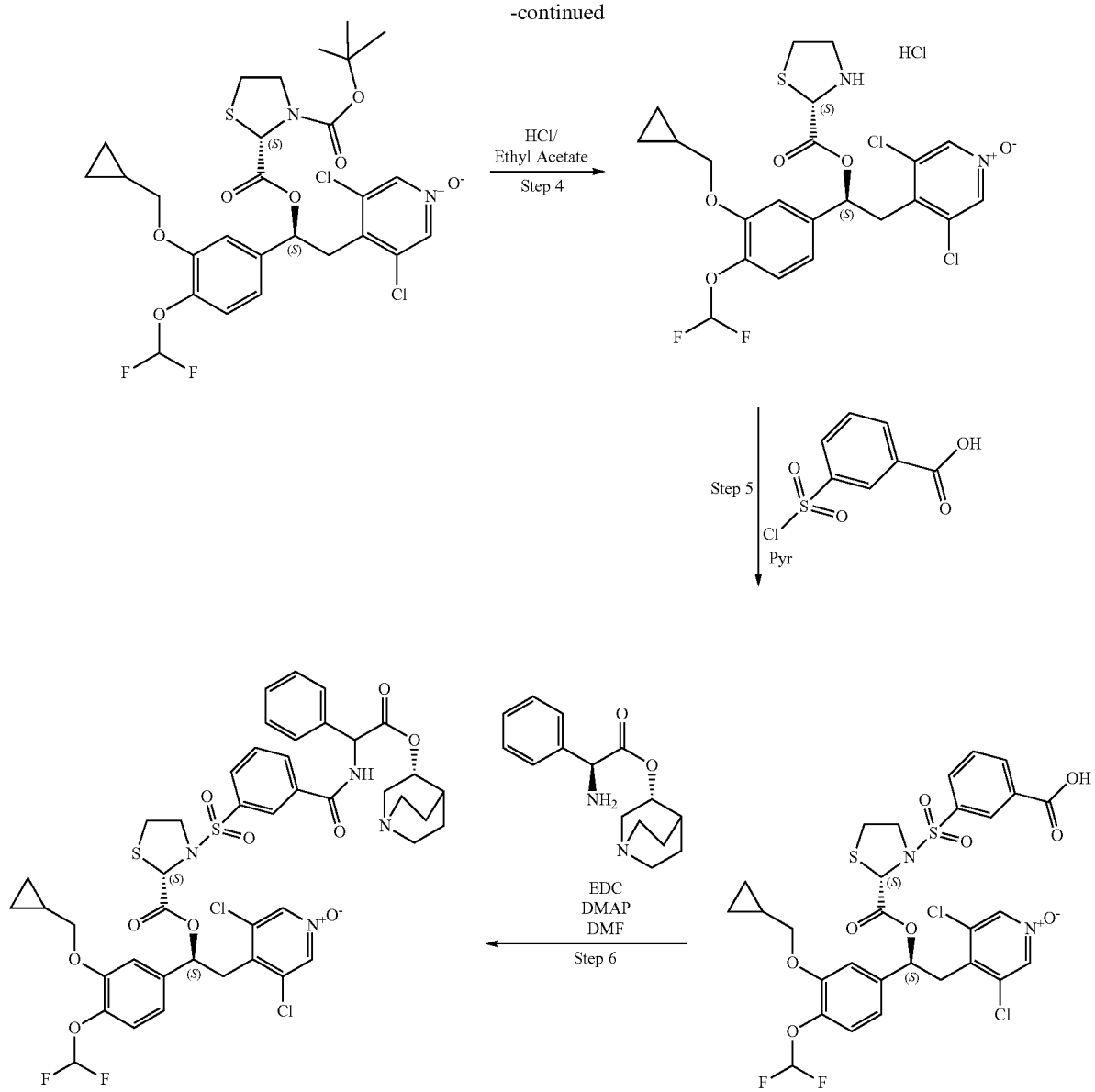

-continued

Step 1: Synthesis of (S)—((R)-quinuclidin-3-yl) 2-(tert-butoxycarbonylamino)-2-phenylacetate (Intermediate 1)

(S)-2-(tert-butoxycarbonylamino)-2-phenylacetic acid (2 g, 7.96 mmol) was dissolved in CH₃CN (20 ml). Di(1H-imidazol-1-yl)methanone (1.936 g, 11.94 mmol) was added, and the reaction was stirred at RT for 1 hour. (R)-quinuclidin-3-ol (1.518 g, 11.94 mmol) was added, and the reaction was stirred at RT for 3 hours to achieve completion. The solvent was removed under vacuum to give a solid that was dissolved in ethyl acetate (300 ml). The precipitate was filtered, and the organic solution was washed with 60 ml of K2CO3 30%, dried over Na2SO4 and evaporated under vacuum to give a crude, that was crystallized in ethyl acetate to give (S)—((R)-quinuclidin-3-yl) 2-(tert-butoxycarbonylamino)-2-phenylacetate (1.67 g, 5.2 mmol).

MS/ESI⁺ 361.0 [MH]⁺

Step 2: Synthesis of (S)—((R)-quinuclidin-3-yl) 2-amino-2-phenylacetate dihydrochloride (Intermediate 2)

(S)—((R)-quinuclidin-3-yl) 2-(tert-butoxycarbonylamino)-2-phenylacetate (0.618 g, 1.715 mmol) was dissolved in THF (6 ml). HCl/dioxane 4M (3 ml, 1.715 mmol) was added, and the reaction was stirred at RT for 30 minutes. The precipitate was filtered, washed with Et2O (10 ml) and dried at RT to give (S)—((R)-quinuclidin-3-yl) 2-amino-2-phenylacetate dihydrochloride (550 mg, 1.65 mmol).

MS/ESI⁺ 261.0 [MH]⁺

Step 3: Synthesis of 4-((S)-2-((S)-3-(tert-butoxycarbonyl)thiazolidine-2-carbonyloxy)-2-(3-(cyclopropylmethoxy)-4-(difluoromethoxy)phenyl)ethyl)-3,5-dichloropyridine 1-oxide (Intermediate 3)

(S)-3,5-dichloro-4-(2-(3-(cyclopropylmethoxy)-4-(difluoromethoxy)phenyl)-2-hydroxyethyl)pyridine 1-oxide (obtained following the procedure described in patent application WO2010/089107, which is incorporated herein by reference in its entirety, 843 mg, 2.006 mmol), (S)-3-(tert-butoxycarbonyl)thiazolidine-2-carboxylic acid (749 mg, 3.21 mmol), DMAP (245 mg, 2.006 mmol), and EDC (1154 mg, 6.02 mmol) were dissolved in DMF (10 ml). The reaction was stirred at RT for 2 hours to achieve completion. The reaction mixture was diluted with Water, and the precipitate was washed with water, dissolved in AcOEt and extracted with HCl 1N, Na2CO3 sat and brine. The organic phase was dried over Na2SO4 and concentrated under vacuum to give 4-((S)-2-((S)-3-(tert-butoxycarbonyl)thiazolidine-2-carbonyloxy)-2-(3-(cyclopropylmethoxy)-4-(difluoromethoxy)phenyl)ethyl)-3,5-dichloropyridine 1-oxide (1.2 g, 1.888 mmol, 94% yield)

MS/ESI+ 635.2 [MH]+

Step 4: Synthesis of 3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide hydrochloride (Intermediate 4)

4-((S)-2-((S)-3-(tert-butoxycarbonyl)thiazolidine-2-carbonyloxy)-2-(3-(cyclopropylmethoxy)-4-(difluoromethoxy)phenyl)ethyl)-3,5-dichloropyridine 1-oxide (4.22 g, 6.64 mmol) was dissolved in ethyl acetate (10 ml). HCl/ethyl acetate 4.2 M (50 ml) was added, and the reaction was stirred at RT for 5 minutes. A white precipitate formed, and it was filtered, washed with ethyl acetate (2×) and hexane and dried in the vacuum oven to yield 3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide hydrochloride (3.19 g, 5.6 mmol, 84% Yield)

$^1$H NMR (400 MHz, DMSO-d$_6$) δ ppm 8.57 (s, 2H), 7.19 (d, J=7.94 Hz, 1H), 7.12 (d, J=1.76 Hz, 1H), 7.08 (t, J=75.00 Hz, 1H), 6.93-7.00 (m, 1H), 5.89-5.98 (m, 1H), 5.12 (s, 1H), 3.91 (d, J=7.06 Hz, 2H), 3.37-3.47 (m, 1H), 3.10-3.31 (m, 3H), 2.77-2.93 (m, 2H), 1.05-1.36 (m, 1H), 0.51-0.63 (m, 2H), 0.34 (d, J=4.85 Hz, 2H).

MS/ESI+ 535.2 [MH]+

Step 5: Synthesis of 4-((S)-2-((S)-3-(3-carboxyphenylsulfonyl)thiazolidine-2-carbonyloxy)-2-(3-(cyclopropylmethoxy)-4-(difluoromethoxy)phenyl)ethyl)-3,5-dichloropyridine 1-oxide (Intermediate 5)

3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide (209 mg, 0.390 mmol) was dissolved in pyridine (4 ml). 3-(chlorosulfonyl)benzoic acid (172 mg, 0.781 mmol) was added slowly at 0° C., and the reaction was stirred at RT for 8 hours. The reaction mixture was diluted with HCl 1N, filtered, and the precipitate was dissolved in DCM. The organic phase was washed with HCl 1N (2×) and brine, dried over Na2SO4 and concentrated under vacuum to give 4-((S)-2-((S)-3-(3-carboxyphenylsulfonyl)thiazolidine-2-carbonyloxy)-2-(3-(cyclopropylmethoxy)-4-(difluoromethoxy)phenyl)ethyl)-3,5-dichloropyridine 1-oxide (100 mg, 0.139 mmol, 35.6% yield), that was used in the next step without any further purification.

MS/ESI+ 719.04 [MH]+

Step 6: Synthesis of [(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[2-oxo-1-phenyl-2-[(3R)-quinuclidin-3-yl]oxy-ethyl]carbamoyl]phenyl]sulfonylthiazolidine-2-carboxylate formate salt (Example 1)

4-((S)-2-((S)-3-(3-carboxyphenylsulfonyl)thiazolidine-2-carbonyloxy)-2-(3-(cyclopropylmethoxy)-4-(difluoromethoxy)phenyl)ethyl)-3,5-dichloropyridine 1-oxide (100 mg, 0.139 mmol), (R)-quinuclidin-3-yl 2-amino-2-phenylacetate (72.4 mg, 0.278 mmol), EDC (53.3 mg, 0.278 mmol), and DMAP (20.37 mg, 0.167 mmol) were dissolved in DMF (2 ml). The reaction was stirred at RT overnight to achieve completion. The reaction mixture was diluted with water and extracted with DCM. The organic phase was dried over Na$_2$SO$_4$ and concentrated under vacuum. The crude was purified by preparative HPLC to give [(1S)-1-[3-(cyclopropylmethoxy)-4-(difluoromethoxy)phenyl]-2-(3,5-dichloro-1-oxido-pyridin-1-ium-4-yl)ethyl](2S)-2-carboxylate formate salt as a mixture of diastereoisomers (20 mg, 0.021 mmol, 14.96% yield).

$^1$H NMR (400 MHz, DMSO-d$_6$) δ ppm 9.48-9.63 (m, 1H), 8.63 (s, 2H), 8.34-8.43 (m, 1H), 8.25 (m, 1H), 8.19 (s, 1H), 8.01-8.11 (m, 1H), 7.83 (m, 1H), 7.59 (m, 2H), 7.42 (d, J=7.50 Hz, 3H), 7.15-7.22 (m, 1H), 7.13 (m., 1H), 7.08 (t, J=75.00 Hz, 1H), 6.92-6.99 (m, 1H), 5.93-6.08 (m, 1H), 5.60-5.72 (m, 1H), 5.54 (s, 1H), 4.67-4.85 (m, 1H), 3.94 (m, 2H), 3.75-3.86 (m, 1H), 3.63-3.74 (m, 1H), 3.44 (m, 4H), 2.92-3.15 (m, 2H), 2.59 (m, 4H), 1.73-1.81 (m, 1H), 1.40-1.67 (m, 3H), 1.13-1.38 (m, 3H), 0.61 (d, J=8.38 Hz, 2H), 0.24-0.40 (m, 2H)

MS/ESI+ 961.18 [MH]+

The following intermediates were synthesized via a similar method as that described in Step 3, starting from (S)-3,5-dichloro-4-(2-(3,4-dimethoxyphenyl)-2-hydroxy ethyl)pyridine 1-oxide, synthesized as described in WO 2012/168226, which is incorporated herein by reference in its entirety.

| Structure | Example number | Analytical Data |
|---|---|---|
| 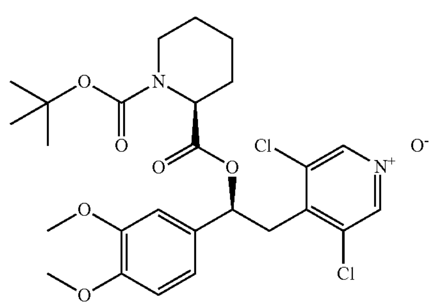 | Intermediate 6 | $^1$H NMR (400 MHz, CDCl$_3$): δ 8.14 (s, 2 H), 6.91-6.76 (m, 3 H), 6.06 (dd, J = 8.9, 5.3 Hz, 1 H), 4.87* (d, J = 5.5 Hz, 1 H), 4.68† (d, J = 5.7 Hz, 1 H), 3.89 (s, 3 H), 3.88 (s, 3 H), 3.53 (dd, J = 13.9, 9.0 Hz, 1 H), 3.26 (dd, J = 13.8, 5.4 Hz, 1 H), 2.86-2.70 (m, 1 H), 2.20 (t, J = 12.6 Hz, 1 H), 1.71-1.48 (m, 5 H), 1.46* (s, 9 H), 1.35† (s, 9 H), 1.02 (qt, J = 13.2, 3.4 Hz, 1 H). * and † refer to different rotamers. [MH+] = 555 |

-continued

| Structure | Example number | Analytical Data |
|---|---|---|
| (structure) | Intermediate 7 | $^1$H NMR (400 MHz, CDCl$_3$): δ 8.14 (s, 2 H), 6.93-6.78 (m, 3 H), 6.10 (dd, J = 9.5, 5.1 Hz, 1 H), 4.85-4.31 (m, 3 H), 3.93-3.86 (m, 6 H), 3.57 (dd, J = 13.8, 10.2 Hz, 1 H), 3.33-3.18 (m, 2 H), 3.12-3.02 (m, 1 H), 1.47* (s, 9 H), 1.28† (s, 9 H). * and † refer to different rotamers. [MH+] = 559 |
| (structure) | Intermediate 8 | $^1$H NMR (400 MHz, CDCl$_3$): δ 8.14* (s, 2 H), 8.13† (s, 2 H), 6.94-6.76 (m, 3 H), 6.05 (ddd, J = 17.6, 9.0, 5.4 Hz, 1 H), 4.32-4.17 (m, 1 H), 3.92-3.83 (m, 6 H), 3.60-3.18 (m, 4 H), 2.26-2.05 (m, 1 H), 1.87-1.71 (m, 3 H), 1.43* (s, 9 H), 1.24† (s, 9 H). * and † refer to different rotamers. [MH+] = 541 |
| (structure) | Intermediate 9 | $^1$H NMR (400 MHz, CDCl$_3$): δ 8.15 (s, 2 H), 6.91-6.82 (m, 3 H), 6.07 (dd, J = 9.3, 4.9 Hz, 1 H), 4.10-3.93 (m, 4 H), 3.90 (s, 3 H), 3.88 (s, 3 H), 3.56 (dd, J = 13.9, 9.3 Hz, 1 H), 3.33-3.23 (m, 2 H), 1.43 (s, 9 H). [MH+] = 527 |

The following intermediates were synthesized via a similar method as that described in Step 4:

| Structure | Example number | Precursor | Analytical Data |
|---|---|---|---|
| (structure) | Intermediate 10 | Intermediate 6 | [MH+] = 455 |

| Structure | Example number | Precursor | Analytical Data |
|---|---|---|---|
| (structure) | Intermediate 11 | Intermediate 7 | [MH+] = 459 |
| (structure) | Intermediate 12 | Intermediate 8 | [MH+] = 441 |

Intermediate 13. [(1S)-2-(3,5-dichloro-1-oxido-pyridin-1-ium-4-yl)-1-(3,4-dimethoxyphenyl)ethyl]azetidine-3-carboxylate hydrochloride (I13)

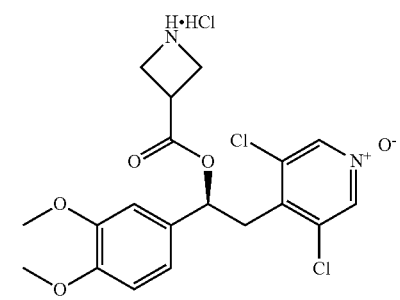

To a stirred solution of (S)-4-(2-((1-(tert-butoxycarbonyl)azetidine-3-carbonyl)oxy)-2-(3,4-dimethoxyphenyl)ethyl)-3,5-dichloropyridine 1-oxide (105 mg, 0.2 mmol) in ethyl acetate (0.5 mL) was added a 2M solution of HCl in diethyl ether (1.5 mL, 3 mmol). The mixture was allowed to stir at room temperature for 4 hours and then acetonitrile (5 mL) was added. The mixture was allowed to stir at room temperature for 3 hours. The solid was removed by filtration, washed with diethyl ether and dried to afford the title compound as a yellow solid (93 mg, 95%).

[MH+]=427

The compound herebelow reported was prepared according to synthetic procedures described in Example 1 as a mixture of diastereoisomers starting from (S)-3,5-dichloro-4-(2-(3,4-dimethoxyphenyl)-2-hydroxyethyl)pyridine 1-oxide, synthesized as described in WO2012/168226, which is incorporated herein by reference in its entirety.

| Structure | Compound | Analytical Data |
|---|---|---|
| 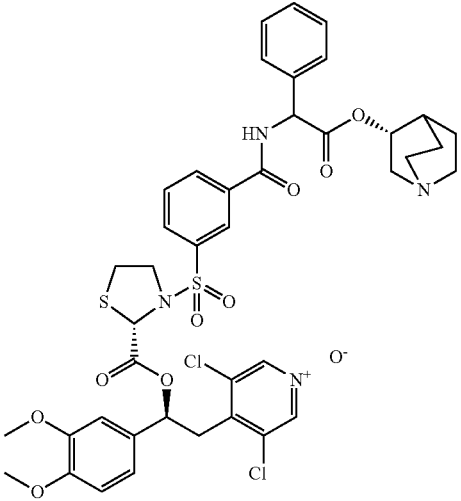<br>[(1S)-2-(3,5-dichloro-1-oxido-pyridin-1-ium-4-yl)-1-(3,4-dimethoxyphenyl)ethyl](2S)-3-[3-[[2-oxo-1-phenyl-2-[(3R)-quinuclidin-3-yl]oxy-ethyl]carbamoyl]phenyl]sulfonylthiazolidine-2-carboxylate formate salt | Example 2 | $^1$H NMR (400 MHz, DMSO) δ ppm 9.57 (dd, J = 6.50, 3.64 Hz, 1 H), 8.57 (d, J = 3.75 Hz, 2 H), 8.39 (d, J = 4.85 Hz, 1 H), 8.27 (d, J = 7.06 Hz, 1 H), 8.06 (d, J = 7.50 Hz, 1 H), 7.70-7.84 (m, 1 H), 7.50-7.59 (m, 2 H), 7.29-7.48 (m, 3 H), 6.81-6.97 (m, 3 H), 5.89-6.11 (m, 1 H), 5.68 (s, 1 H), 5.47 (s, 1 H), 4.70-4.90 (m, 1 H), 3.62-3.99 (m, 10 H), 3.47 (dd, J = 14.11, 9.26 Hz, 1 H), 2.87-3.09 (m, 2 H), 2.55-2.69 (m, 5 H), 1.73-1.87 (m, 1 H), 1.09-1.68 (m, 4 H). MS/ESI$^+$ [MH]$^+$ 884.9 |

Example 3

[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[(N-[(3R)-quinuclidin-3-yl]oxycarbonylanilino)methyl]benzoyl]thiazolidine-2-carboxylate formate salt (E3)

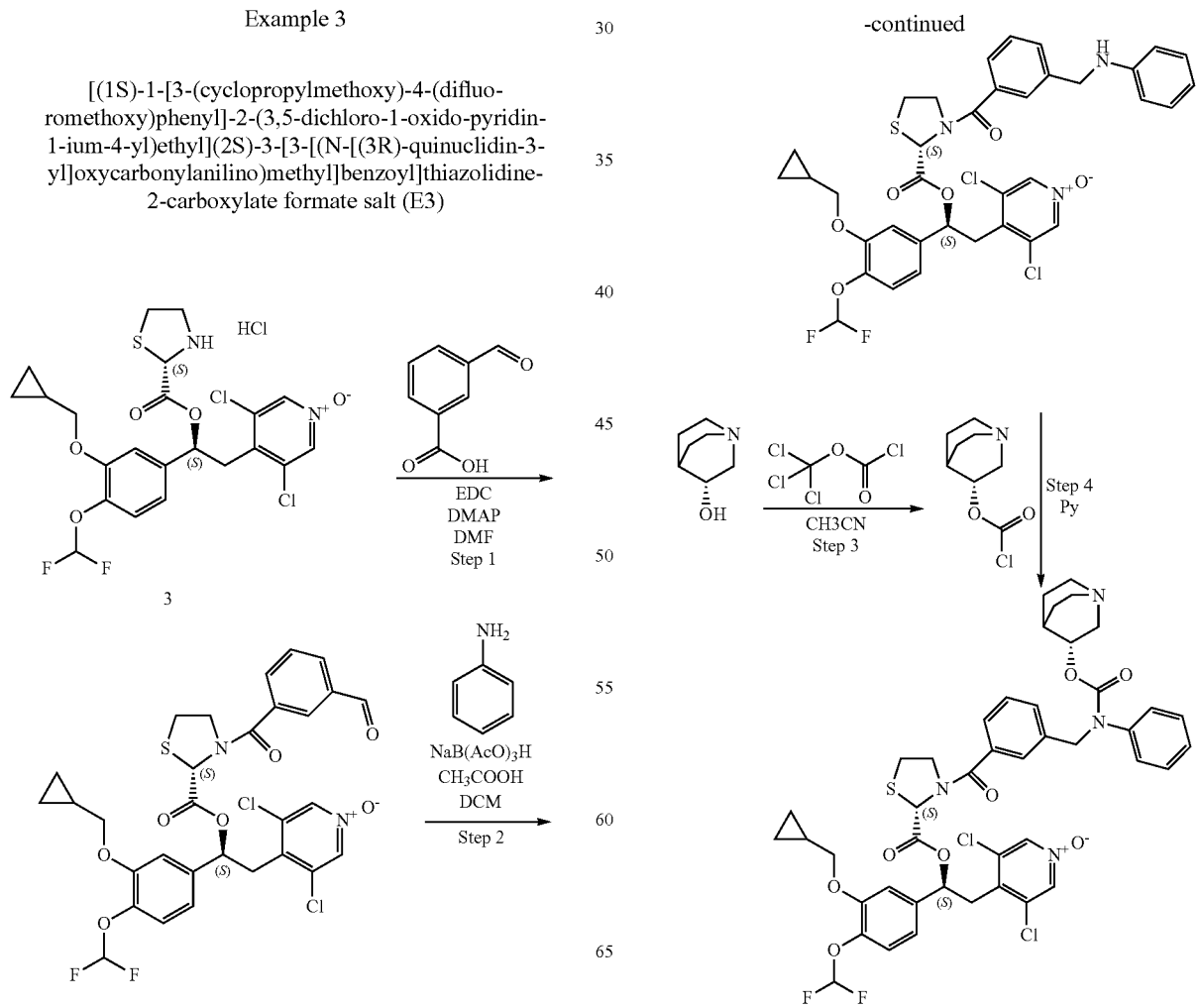

Step 1: Synthesis of 3,5-dichloro-4-((S)-2-(3-(cyclopropylmethoxy)-4-(difluoromethoxy)phenyl)-2-((S)-3-(3-formylbenzoyl)thiazolidine-2-carbonyloxy)ethyl)pyridine 1-oxide (Intermediate 14)

3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide (Int 4, 208 mg, 0.389 mmol), 3-formylbenzoic acid (87 mg, 0.583 mmol), EDC (149 mg, 0.777 mmol), and DMAP (57.0 mg, 0.466 mmol) were dissolved in DMF (2 ml). The reaction was stirred at RT for 8 hours to achieve completion. The reaction mixture was diluted with HCl 1N, and the precipitate was filtered, washed with HCl 1N, dissolved in DCM and extracted with HCl 1N, Na$_2$CO$_3$ sat and brine. The organic phase was dried over Na$_2$SO$_4$ and concentrated under vacuum to give 3,5-dichloro-4-((S)-2-(3-(cyclopropylmethoxy)-4-(difluoromethoxy)phenyl)-2-((S)-3-(3-formylbenzoyl)thiazolidine-2-carbonyloxy)ethyl)pyridine 1-oxide (108 mg, 0.162 mmol, 41.6% yield). The compound was used in the next step without any further purification.

MS/ESI$^+$ 667.08 [MH]$^+$

Step 2: Synthesis of 3,5-dichloro-4-((S)-2-(3-(cyclopropylmethoxy)-4-(difluoromethoxy)phenyl)-2-((S)-3-(3-((phenylamino)methyl)benzoyl)thiazolidine-2-carbonyloxy)ethyl)pyridine 1-oxide (Intermediate 15)

3,5-dichloro-4-((S)-2-(3-(cyclopropylmethoxy)-4-(difluoromethoxy)phenyl)-2-((S)-3-(3-formylbenzoyl)thiazolidine-2-carbonyloxy)ethyl)pyridine 1-oxide (108 mg, 0.162 mmol) was dissolved in DCM (2 ml). Aniline (18.08 mg, 0.194 mmol) and acetic acid (9.26 µL, 0.162 mmol) were added, and the mixture was stirred at RT for 1 hour. Sodium triacetoxyborohydride (51.4 mg, 0.243 mmol) was added, and the mixture was stirred at RT overnight to achieve completion. The reaction mixture was diluted with DCM and extracted with water (2×). The organic phase was dried over Na$_2$SO$_4$ and concentrated under vacuum to give 3,5-dichloro-4-((S)-2-(3-(cyclopropylmethoxy)-4-(difluoromethoxy)phenyl)-2-((S)-3-(3-((phenylamino)methyl)benzoyl)thiazolidine-2-carbonyloxy)ethyl)pyridine 1-oxide (120 mg, 0.161 mmol, 100% yield). The compound was used in the next step without any further purification.

MS/ESI$^+$ 743.14 [MH]$^+$

Step 3: Synthesis of (R)-Quinuclidin-3-yl carbonochloridate hydrochloride (Intermediate 16)

To a stirred solution of (R)-3-quinuclidinol (2.5 g, 19.66 mmol) in acetonitrile (200 mL) was added trichloromethyl chloroformate (3.06 mL, 25.57 mmol) dropwise at 0° C., and the mixture was allowed to stir at 0° C. for 1 hour. The reaction mixture was then stirred at RT for 16 hours, and then the solvent was removed in vacuo to afford the title compound as a white solid (4.39 g, 98%).

$^1$H NMR (400 MHz, DMSO-d$_6$): δ 10.29 (s, 1H), 4.05-3.95 (m, 1H), 3.43 (t, J=10.8 Hz, 1H), 3.12 (m, 3H), 3.10-2.95 (m, 1H), 2.79 (d, J=13.3 Hz, 1H), 2.12-2.02 (m, 1H), 1.98 (m, J=3.4 Hz, 1H), 1.89-1.78 (m, 1H), 1.75-1.59 (m, 2H).

Step 4: Synthesis of [(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[(N-[(3R)-quinuclidin-3-yl]oxycarbonylanilino)methyl]benzoyl]thiazolidine-2-carboxylate formate salt (Example 3)

3,5-dichloro-4-((S)-2-(3-(cyclopropylmethoxy)-4-(difluoromethoxy)phenyl)-2-((S)-3-(3-((phenylamino)methyl)benzoyl)thiazolidine-2-carbonyloxy)ethyl)pyridine 1-oxide (120 mg, 0.161 mmol) was dissolved in Pyridine (1 ml, 12.36 mmol). (R)-quinuclidin-3-yl carbonochloridate (76 mg, 0.403 mmol) was added under N$_2$ atmosphere and at 0° C. The reaction was stirred at RT for two days to achieve completion. The reaction mixture was diluted with HCl 1N and the precipitate was filtered, washed with Water and purified by preparative HPLC to give 3,5-dichloro-4-((S)-2-(3-(cyclopropylmethoxy)-4-(difluoromethoxy)phenyl)-2-((S)-3-(3-((phenyl(((R)-quinuclidin-3-yloxy)carbonyl)amino)methyl)benzoyl)thiazolidine-2-carbonyloxy)ethyl)pyridine 1-oxide formate salt (20 mg, 0.022 mmol, 13.82% yield).

$^1$H NMR (400 MHz, DMSO-d$_6$) δ ppm 8.54 (s, 2H), 8.19 (s, 2H), 6.84-7.53 (m, 13H), 5.99 (m, 1H), 5.51 (s, 1H), 4.93 (s, 2H), 4.66 (m, 1H), 3.84 (d, J=6.62 Hz, 2H), 3.53-3.75 (m, 4H), 3.08 (m, 6H), 2.60 (m, 2H), 1.83 (m, 1H), 1.34-1.62 (m, 2H), 1.16 (m, 4H), 0.52 (d, J=7.50 Hz, 2H), 0.26 (m, 2H)

MS/ESI$^+$ 897.22 [MH]$^+$

The compounds herebelow reported were prepared according to synthetic procedures as described in Example 3, starting from (S)-3,5-dichloro-4-(2-(3,4-dimethoxyphenyl)-2-hydroxyethyl)pyridine 1-oxide, synthesized as described in WO2012/168226, which is incorporated herein by reference in its entirety.

| Structure | Compound | Analytical Data |
|---|---|---|
| 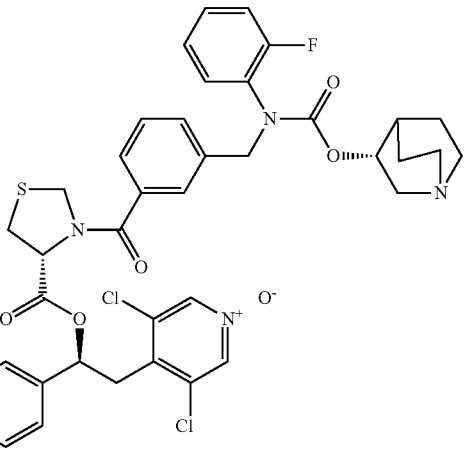<br>[(1S)-2-(3,5-dichloro-1-oxido-pyridin-1-ium-4-yl)-1-(3,4-dimethoxyphenyl)ethyl](4R)-3-[3-[(2-fluoro-N-[(3R)-quinuclidin-3-yl]oxycarbonyl-anilino)methyl]benzoyl]thiazolidine-4-carboxylate | Example 4 | $^1$H NMR (400 MHz, DMSO) δ 8.34 (s, 2 H), 7.43-7.12 (m, 8 H), 7.00-6.88 (m, 3 H), 6.05 (dd, J = 8.6, 5.2 Hz, 1 H), 5.03-4.97 (m, 1 H), 4.85 (s, 2 H), 4.73-4.67 (m, 1 H), 4.55 (d, J = 9.3 Hz, 1 H), 4.39 (d, J = 9.3 Hz, 1 H), 3.79 (s, 3 H), 3.75 (s, 3 H), 3.55-3.40 (m, 2 H), 3.30 (dd, J = 14.5, 5.0 Hz, 1 H), 3.15-3.04 (m, 2 H), 2.70-2.54 (m, 4 H), 2.49-2.43 (m, 1 H), 1.88-1.83 (m, 1 H), 1.62-1.53 (m, 1 H), 1.52-1.42 (m, 1 H), 1.39-1.28 (m, 1 H), 1.24-1.14 (m, 1 H). MS/ESI$^+$ 839 [MH]$^+$ |
| 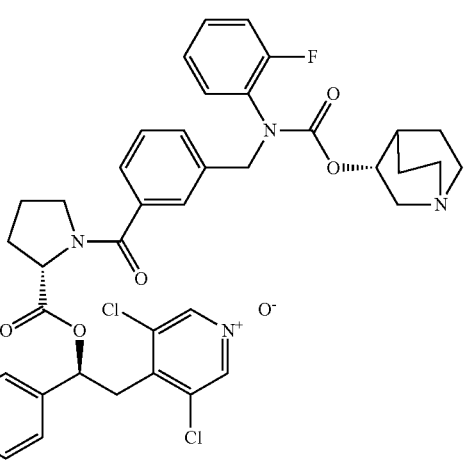<br>[(1S)-2-(3,5-dichloro-1-oxido-pyridin-1-ium-4-yl)-1-(3,4-dimethoxyphenyl)ethyl](2S)-1-[3-[(2-fluoro-N-[(3R)-quinuclidin-3-yl]oxycarbonyl-anilino)methyl]benzoyl]pyrrolidine-2-carboxylate | Example 5 | $^1$H NMR (400 MHz, DMSO) δ 8.34 (s, 2 H), 7.38-7.10 (m, 8 H), 6.96-6.86 (m, 3 H), 6.02 (dd, J = 9.0, 5.5 Hz, 1 H), 4.84 (s, 2 H), 4.73-4.68 (m, 1 H), 4.49 (dd, J = 8.5, 4.3 Hz, 1 H), 3.82-3.75 (m, 1 H), 3.79 (s, 3 H), 3.72 (s, 3 H), 3.53-3.44 (m, 1 H), 3.41 (t, J = 6.8 Hz, 2 H), 3.28 (dd, J = 14.2, 5.7 Hz, 1 H), 3.09 (ddd, J = 14.9, 8.2, 2.5 Hz, 1 H), 2.68-2.55 (m, 3 H), 2.36-2.22 (m, 2 H), 1.90-1.73 (m, 4 H), 1.63-1.53 (m, 1 H), 1.53-1.42 (m, 1 H), 1.40-1.29 (m, 1 H), 1.26-1.14 (m, 1 H). MS/ESI$^+$ 821 [MH]$^+$ |

| Structure | Compound | Analytical Data |
|---|---|---|
| 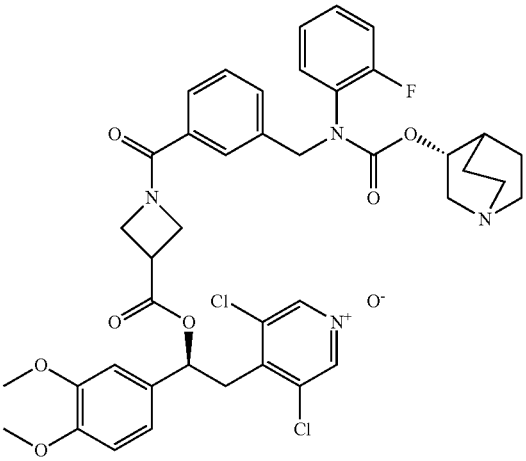<br>[(1S)-2-(3,5-dichloro-1-oxido-pyridin-1-ium-4-yl)-1-(3,4-dimethoxyphenyl)ethyl]1-[3-[(2-fluoro-N-[(3R)-quinuclidin-3-yl]oxycarbonyl-anilino)methyl]benzoyl]azetidine-3-carboxylate | Example 6 | $^1$H NMR (400 MHz, DMSO): δ 8.53 (s, 2 H), 7.52-7.10 (m, 8 H), 6.97-6.87 (m, 3 H), 6.02-5.94 (m, 1 H), 4.86 (s, 2 H), 4.69-4.61 (m, 1 H), 4.40-4.29 (m, 1 H), 4.25-4.08 (m, 2 H), 3.98-3.89 (m, 1 H), 3.75 (s, 6 H), 3.59-3.44 (m, 1 H), 3.29-3.20 (m, 1 H), 3.11-2.99 (m, 2 H), 2.64-2.32 (m, 5 H), 1.85-1.73 (m, 1 H), 1.57-1.47 (m, 1 H), 1.47-1.36 (m, 1 H), 1.19-1.07 (m, 2 H). MS/ESI$^+$ 807 [MH]$^+$ |

Example 7

Synthesis of [(1S)-2-(3,5-dichloro-1-oxido-pyridin-1-ium-4-yl)-1-(3,4-dimethoxyphenyl)ethyl](2S)-1-[3-[(2-fluoro-N-[(3R)-quinuclidin-3-yl]oxycarbonyl-anilino)methyl]benzoyl]piperidine-2-carboxylate (E7)

Step 1: Synthesis of methyl 3-[(2-fluoroanilino)methyl]benzoate (Intermediate 17)

To a stirred solution of methyl 3-formylbenzoate (1 g, 6.092 mmol) in anhydrous DCM (30 mL) was added 2-fluoroaniline (0.620 mL, 6.396 mmol) followed by glacial acetic acid (0.350 mL, 6.092 mmol). The reaction was stirred at

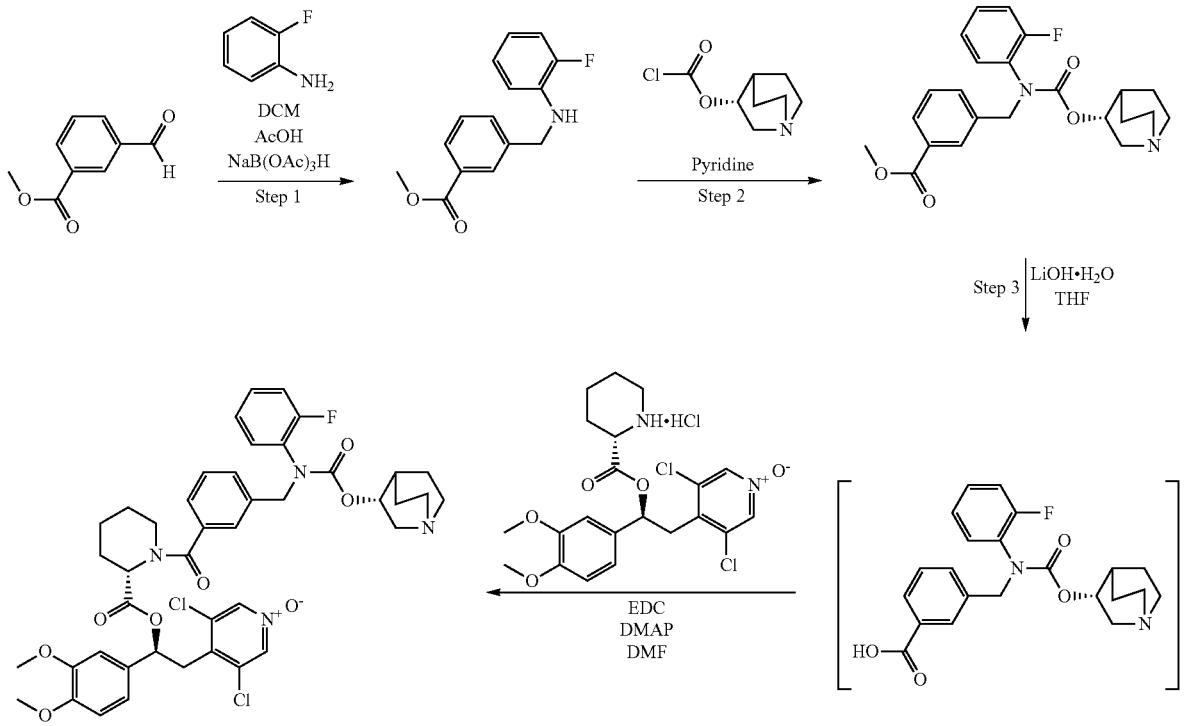

room temperature for 18 hours. Sodium triacetoxyborohydride (3.23 g, 15.23 mmol) was added, and the reaction was stirred at room temperature for 3 hours. Water was added to quench the reaction, and the mixture was diluted with DCM. The organic layer was washed with brine, passed through a hydrophobic frit and the solvent was removed in vacuo to afford the title compound as a yellow oil (1.57 g, quantitative yield).

MS/ESI+ 413.2 [MH]+

Step 2: Synthesis of methyl 3-[(2-fluoro-N-[(3R)-quinuclidin-3-yl]oxycarbonyl-anilino)methyl]benzoate (Intermediate 18)

To a stirred solution of methyl 3-[(2-fluoroanilino)methyl]benzoate (0.3 g, 1.157 mmol) in anhydrous pyridine (6 mL) at 0° C. under $N_2$ (g) was added 4-(dimethylamino)pyridine (0.014 g, 0.116 mmol) followed by (R)-quinuclidin-3-yl carbonochloridate hydrochloride (0.314 g, 1.39 mmol) in one portion. After stirring at 0° C. for 1 hour, the reaction was allowed to warm to room temperature. After 2.5 hours, further (R)-quinuclidin-3-yl carbonochloridate (0.628 g, 2.777 mmol) was added, and the reaction was stirred at room temperature for 65 hours. The reaction was quenched by addition of 10% aqueous potassium carbonate solution and extracted with ethyl acetate (×3). The combined organic extracts were washed with brine and dried (sodium sulfate), filtered, and the solvent was removed in vacuo to afford a brown oil. The crude material was purified by silica gel column chromatography eluting sequentially with ethyl acetate, 5% methanol in ethyl acetate, 5% 7N methanolic ammonia in ethyl acetate and 10% 7N methanolic ammonia in ethyl acetate to afford the title compound as a yellow oil (0.349 g, 73%).

¹H NMR (400 MHz, CDCl3): δ 7.97-7.86 (m, 2H), 7.53-7.45 (m, 1H), 7.37 (t, J=7.7 Hz, 1H), 7.27-7.19 (m, 1H), 7.16-6.96 (m, 3H), 4.90-4.74 (m, 3H), 3.89 (s, 3H), 3.24-3.14 (m, 1H), 2.84-2.53 (m, 5H), 1.96-1.83 (m, 1H), 1.66-1.36 (m, 3H), 1.33-1.13 (m, 1H).

Step 3: Synthesis of [(1S)-2-(3,5-dichloro-1-oxido-pyridin-1-ium-4-yl)-1-(3,4-dimethoxyphenyl)ethyl](2S)-1-[3-[(2-fluoro-N-[(3R)-quinuclidin-3-yl]oxycarbonyl-anilino)methyl]benzoyl]piperidine-2-carboxylate (Example 7)

To a stirred solution of methyl 3-[(2-fluoro-N-[(3R)-quinuclidin-3-yl]oxycarbonyl-anilino)methyl]benzoate (4.12 g, 10 mmol) in tetrahydrofuran (45 mL) and methanol (45 mL) was added lithium hydroxide hydrate (839 mg, 20 mmol) in water (18 mL), and the mixture was stirred at room temperature for 24 hours. The solvent was removed in vacuo and the residue was purified using an SCX-2 cartridge eluting sequentially with methanol and 7 N methanolic ammonia. The product was triturated with THF (×5) and diethyl ether to give 3-[(2-fluoro-N-[(3R)-quinuclidin-3-yl]oxycarbonyl-anilino)methyl]benzoic acid (3.51 g, 88%) as a white solid.

To a solution of 3-[(2-fluoro-N-[(3R)-quinuclidin-3-yl]oxycarbonyl-anilino)methyl]benzoic acid (76 mg, 0.19 mmol) in DMF (2 mL) was then added [(1S)-2-(3,5-dichloro-1-oxido-pyridin-1-ium-4-yl)-1-(3,4-dimethoxyphenyl)ethyl](2S)-piperidine-2-carboxylate hydrochloride (Int 6, 93 mg, 0.19 mmol), followed by DMAP (11 mg, 0.1 mmol) and EDC (72 mg, 0.37 mmol). The mixture was allowed to stir at room temperature for 5 hours, and then the solvent was removed in vacuo. The residue was partitioned between ethyl acetate (10 mL) and saturated sodium bicarbonate solution (10 mL). The separated organic phase was passed through a hydrophobic frit and the solvent was removed in vacuo. Purification was achieved by preparative HPLC to afford the title compound as a white solid (66 mg, 42%).

¹H NMR (400 MHz, DMSO @110° C.) δ 8.33 (s, 2H), 7.39-7.10 (m, 8H), 6.99-6.87 (m, 3H), 6.10 (t, J=6.7 Hz, 1H), 4.92-4.84 (m, 1H), 4.84 (s, 2H), 4.74-4.66 (m, 1H), 3.80 (s, 3H), 3.78 (s, 3H), 3.75-3.58 (m, 1H), 3.52 (dd, J=14.2, 8.7 Hz, 1H), 3.31 (dd, J=13.9, 5.3 Hz, 1H), 3.08 (dd, J=14.5, 8.0 Hz, 1H), 2.94-2.79 (m, 1H), 2.68-2.42 (m, 5H), 2.17 (d, J=13.7 Hz, 1H), 1.89-1.81 (m, 1H), 1.78-1.26 (m, 7H), 1.24-1.09 (m, 2H)

[MH+]=835

Example 8

[(1S)-2-(3,5-dichloro-1-oxido-pyridin-1-ium-4-yl)-1-(3,4-dimethoxyphenyl)ethyl](2S)-1-[4-[(2-fluoro-N-[(3R)-quinuclidin-3-yl]oxycarbonyl-anilino)methyl]phenyl]sulfonylpyrrolidine-2-carboxylate (E8)

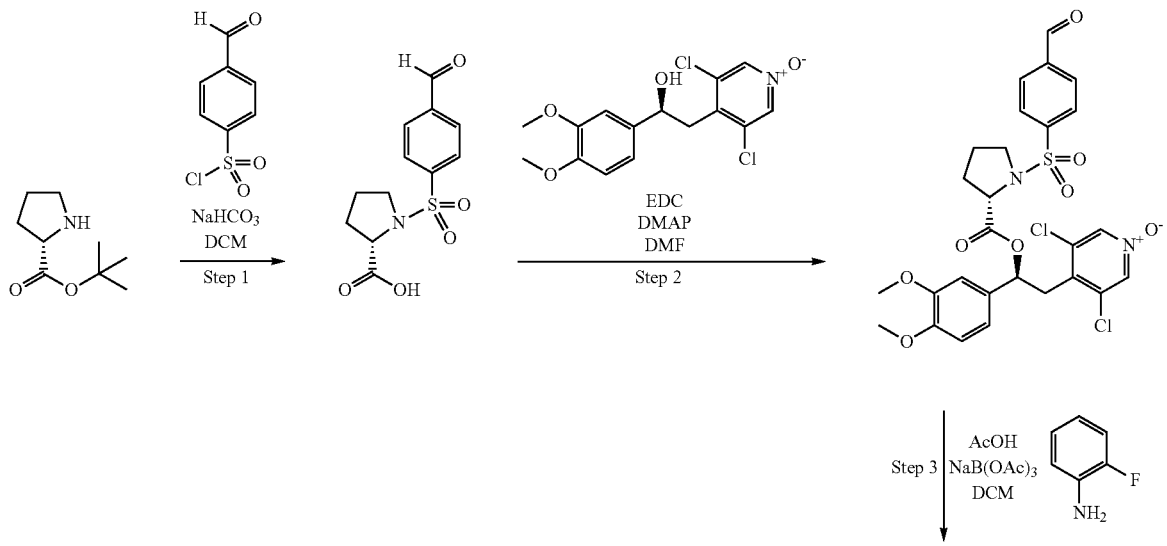

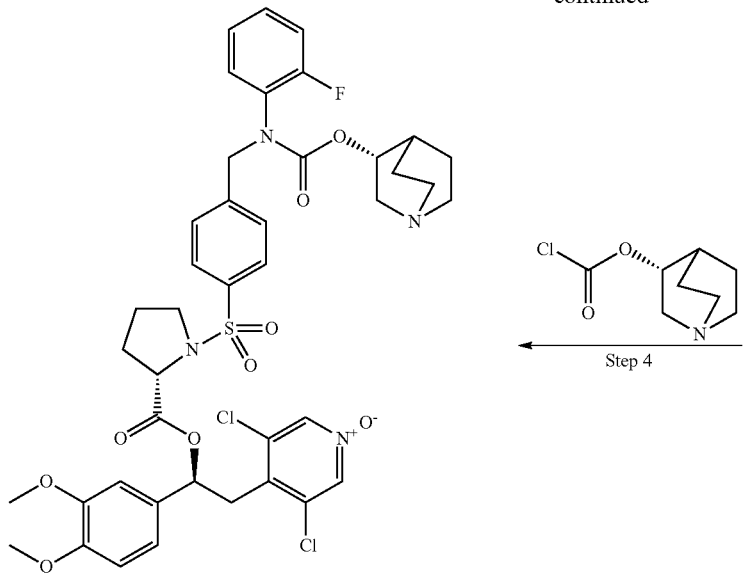
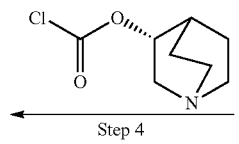
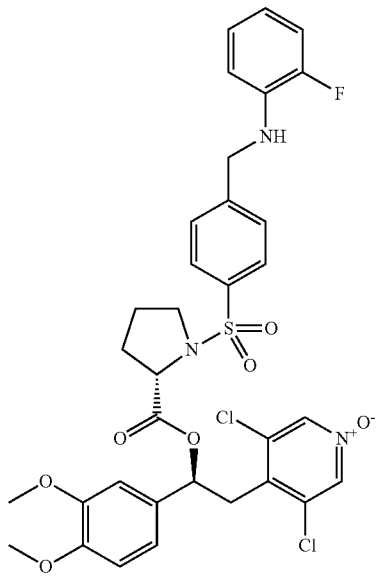

Step 4

Step 1: Synthesis of (2S)-1-(4-formylphenyl)sulfonylpyrrolidine-2-carboxylic acid (Intermediate 19)

To a vigorously stirred solution of 4-formylbenzenesulfonyl chloride (1 g, 5 mmol) in DCM (10 mL), was added saturated aqueous sodium bicarbonate solution (10 mL), followed by tert-butyl(2S)-pyrrolidine-2-carboxylate (856 mg, 5 mmol). The organic phase was passed through a hydrophobic frit, and the solvent was removed in vacuo. The crude material was purified by silica gel column chromatography, eluting with 0-100% EtOAc in isohexane, to afford the title compound as a colourless gum (849 mg, 60%).

$^1$H NMR (400 MHz, CDCl$_3$): δ 10.15 (s, 1H), 8.10 (d, J=8.1 Hz, 2H), 8.02 (d, J=8.1 Hz, 2H), 4.10-3.95 (m, 4H), 3.63 (s, 3H), 3.36-3.25 (m, 1H).

[MH+]=284

Step 2: Synthesis of [(1S)-2-(3,5-dichloro-1-oxido-pyridin-1-ium-4-yl)-1-(3,4-dimethoxyphenyl)ethyl] (2S)-1-(4-formylphenyl)sulfonylpyrrolidine-2-carboxylate (Intermediate 20)

To a stirred solution of (2S)-1-(4-formylphenyl)sulfonylpyrrolidine-2-carboxylic acid (283 mg, 1 mmol) in DMF (15 mL) was added (1S)-2-(3,5-dichloro-1-oxido-pyridin-1-ium-4-yl)-1-(3,4-dimethoxyphenyl)ethanol (344 mg, 1 mmol), followed by DMAP (60 mg, 0.5 mmol) and EDC (385 mg, 2 mmol). The mixture was allowed to stir at room temperature for 18 hours and then the solvent was removed in vacuo. The residue was partitioned between ethyl acetate (15 mL) and saturated sodium bicarbonate solution (15 mL). The organic phase was passed through a hydrophobic fit and the solvent was removed in vacuo. The crude material was purified by silica gel column chromatography, eluting with 0-100% EtOAc in isohexane followed by 10% methanol in DCM, to afford the title compound as an off-white solid (333 mg, 55%).

$^1$H NMR (400 MHz, CDCl$_3$): δ 10.10 (s, 1H), 8.15 (s, 2H), 8.01 (d, J=8.0 Hz, 2H), 7.95 (d, J=8.0 Hz, 2H), 7.00-6.79 (m, 3H), 6.08 (dd, J=9.3, 5.1 Hz, 1H), 4.37 (dd, J=8.7, 3.6 Hz, 1H), 3.91 (s, 3H), 3.88 (s, 3H), 3.60 (dd, J=13.9, 9.3 Hz, 1H), 3.48-3.24 (m, 3H), 1.92-1.72 (m, 4H)

[MH+]=609.

Step 3: Synthesis of [(1S)-2-(3,5-dichloro-1-oxido-pyridin-1-ium-4-yl)-1-(3,4-dimethoxyphenyl)ethyl] (2S)-1-[4-[(2-fluoroanilino)methyl]phenyl]sulfonyl pyrrolidine-2-carboxylate (Intermediate 21)

To a stirred solution of [(1S)-2-(3,5-dichloro-1-oxido-pyridin-1-ium-4-yl)-1-(3,4-dimethoxyphenyl)ethyl](2S)-1-(4-formylphenyl)sulfonylpyrrolidine-2-carboxylate (122 mg, 0.2 mmol) in DCM (1 mL) was added 2-fluoroaniline (0.02 mL, 0.21 mmol) followed by glacial acetic acid (0.01 mL, 0.2 mmol). The reaction was stirred at room temperature for 18 hours. Sodium triacetoxyborohydride (107 mg, 0.51 mmol) was added, and the reaction was stirred at room temperature for 24 hours. DCM (10 mL) and 2 M aqueous HCl (10 mL) was added and the organic phase was passed through a hydrophobic fit and the solvent was removed in vacuo. The crude material was purified by silica gel column chromatography, eluting with 0-100% EtOAc in isohexane, to afford the title compound as an off-white solid (123 mg, 87%).

$^1$H NMR (400 MHz, CDCl$_3$): δ 8.14 (s, 2H), 7.78 (d, J=8.1 Hz, 2H), 7.51 (d, J=8.1 Hz, 2H), 7.04-6.52 (m, 7H), 6.08 (dd, J=9.2, 5.2 Hz, 1H), 4.47 (s, 2H), 4.31 (dd, J=8.7, 3.8 Hz, 1H), 3.91 (s, 3H), 3.88 (s, 3H), 3.60 (dd, J=13.9, 9.3 Hz, 1H), 3.47-3.37 (m, 1H), 3.32-3.15 (m, 2H), 2.06-1.54 (m, 4H).

[MH+]=704

Step 4: Synthesis of [(1S)-2-(3,5-dichloro-1-oxido-pyridin-1-ium-4-yl)-1-(3,4-dimethoxyphenyl)ethyl] (2S)-1-[4-[(2-fluoro-N-[(3R)-quinuclidin-3-yl]oxy carbonyl-anilino)methyl]phenyl]sulfonylpyrrolidine-2-carboxylate (Example 8)

To a stirred solution of [(1S)-2-(3,5-dichloro-1-oxido-pyridin-1-ium-4-yl)-1-(3,4-dimethoxyphenyl)ethyl](2S)-1-[4-[(2-fluoroanilino)methyl]phenyl]sulfonylpyrrolidine-2-carboxylate (105 mg, 0.15 mmol) in acetonitrile (3.2 mL) was added (R)-quinuclidin-3-yl carbonochloridate hydrochloride (131 mg, 0.6 mmol) and pyridine (0.12 mL), and the mixture was heated to 80° C. in a microwave for 6 minutes. Further (R)-quinuclidin-3-yl carbonochloridate hydrochloride (34 mg, 0.15 mmol) was added, and the mixture was heated to 80° C. in a microwave for 6 minutes. The solvent was removed in vacuo and the mixture was partitioned between ethyl acetate (10 mL) and water (10 mL). The layers were separated and the water was removed in vacuo. Purification of the residue from the aqueous layer was achieved by preparative HPLC to afford the title compound as a white solid (21 mg, 16%).

$^{1}$H NMR (400 MHz, DMSO): δ 8.59 (s, 2H), 7.73 (d, J=7.7 Hz, 2H), 7.57-7.15 (m, 6H), 6.99-6.88 (m, 3H), 6.01 (dd, J=9.7, 4.5 Hz, 1H), 4.99-4.85 (m, 2H), 4.70-4.64 (m, 1H), 4.09 (dd, J=8.7, 4.0 Hz, 1H), 3.77 (s, 3H), 3.76 (s, 3H), 3.49 (dd, J=14.3, 9.7 Hz, 1H), 3.35-3.23 (m, 1H), 3.26 (dd, J=14.3, 4.7 Hz, 1H), 3.17-3.03 (m, 2H), 2.76-2.38 (m, 5H), 1.93-1.76 (m, 2H), 1.73-1.38 (m, 6H), 1.22-1.10 (m, 1H).

[MH+]=857

The compounds herebelow reported in the following table were prepared as a mixture of diastereoisomers according to synthetic procedures which would be known to the skilled person.

| Structure | Compound | $^{1}$H NMR |
|---|---|---|
| 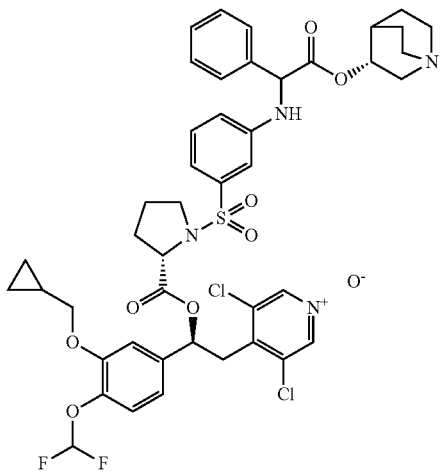 [(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[2-oxo-1-phenyl-2-[(3R)-quinuclidin-3-yl]oxy-ethyl]amino]phenyl]sulfonylpyrrolidine-2-carboxylate trifluoroacetate salt | Example 9 | $^{1}$H NMR (300 MHz, DMSO-d6) δ ppm 9.35 and 9.49 (br. s., 1 H), 8.58 (s, 2 H), 7.50-7.62 (m, 2 H), 7.28-7.49 (m, 4 H), 7.11-7.25 (m, 2 H), 6.88-7.07 (m, 5 H), 7.08 (t, 1 H), 5.93-6.15 (m, 1 H), 5.44 and 5.49 (d, 1 H), 4.90-5.19 (m, 1 H), 3.96-4.15 (m, 1 H), 3.93 (d, 2 H), 3.59-3.75 (m, 1 H), 2.68-3.37 (m, 9 H), 1.84-2.34 (m, 1 H), 0.99-1.82 (m, 9 H), 0.48-0.67 (m, 2 H), 0.22-0.47 (m, 2 H) MS/ESI$^{+}$ 915.23 [MH]$^{+}$ |
| 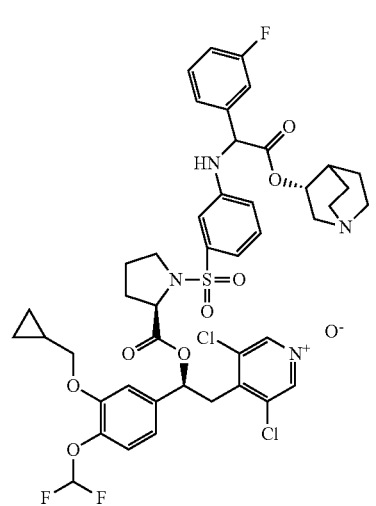 [(1S)-1-[3-(cyclopropylmethoxy)-4-(difluoromethoxy)phenyl]-2-(3,5-dichloro-1-oxido-pyridin-1-ium-4-yl)ethyl](2R)-1-[3-[[1-(3-fluorophenyl)-2-oxo-2-[(3R)-quinuclidin-3-yl]oxy-ethyl]amino]phenyl]sulfonylpyrrolidine-2-carboxylate trifluoroacetate salt | Example 10 | $^{1}$H NMR (300 MHz, DMSO-d6) δ ppm 9.42 and 9.57 (br. s., 1 H), 8.58 (s, 2 H), 7.28-7.56 (m, 4 H), 7.11-7.24 (m, 3 H), 6.75-7.25 (m, 6 H), 6.02 (dd, 1 H), 5.55 and 5.58 (d, 1 H), 4.94-5.17 (m, 1 H), 3.97-4.10 (m, 1 H), 3.92 (d, 2 H), 3.57-3.72 (m, 2 H), 3.39-3.53 (m, 1 H), 2.98-3.36 (m, 5 H), 2.75-2.97 (m, 2 H), 2.00-2.13 and 2.21-2.31 (m, 1 H), 1.07-2.00 (m, 9 H), 0.47-0.70 (m, 2 H), 0.20-0.46 (m, 2 H) MS/ESI$^{+}$ 933.2 [MH]$^{+}$ |

| Structure | Compound | ¹H NMR |
|---|---|---|
| 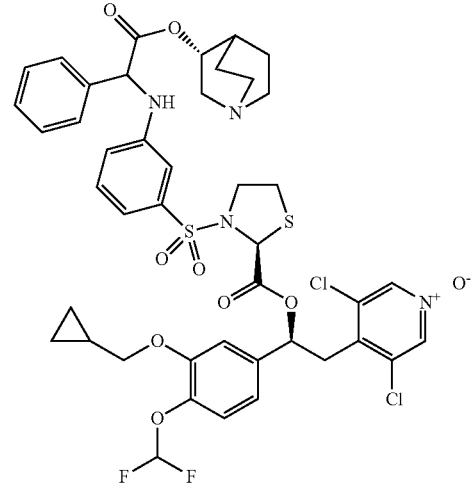<br>[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[2-oxo-1-phenyl-2-[(3R)-quinuclidin-3-yl]oxy-ethyl]amino]phenyl]sulfonylthiazolidine-2-carboxylate trifluoroacetate salt | Example 11 | ¹H NMR (300 MHz, DMSO-d6) δ ppm 9.43 and 9.56 (br. s., 1 H), 8.56 and 8.57 (s, 2 H), 7.49-7.64 (m, 2 H), 7.27-7.49 (m, 4 H), 7.15-7.22 (m, 1 H), 6.76-7.22 (m, 7 H), 5.93-6.19 (m, 1 H), 5.48 and 5.51 (d, 1 H), 5.25 and 5.27 (s, 1 H), 4.97-5.14 (m, 1 H), 3.91 (d, 2 H), 3.56-3.79 (m, 2 H), 3.37-3.56 (m, 1 H), 3.00-3.37 (m, 5 H), 2.58-3.00 (m, 2 H), 2.33-2.45 (m, 2 H), 1.98-2.11 and 2.20-2.31 (m, 1 H), 1.63-1.97 (m, 3 H), 1.39-1.62 (m, 1 H), 1.05-1.33 (m, 1 H), 0.46-0.72 (m, 2 H), 0.19-0.45 (m, 2 H)<br>MS/ESI⁺ 933.2 [MH]⁺ |

Pharmacological Activity of the Compounds of the Invention:

In Vitro Determination of PDE4 Inhibitory Activity:

In vitro determination of PDE4 inhibitory activity for compounds of the invention may be determined according to one of the protocols herebelow reported:

PDE4B2 HTRF Assay:

PDE4B2 activity is detected using the LANCE Ultra cAMP homogeneous time resolved fluorescence resonance energy transfer (TR-FRET) assay from Perkin Elmer. The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 µl. Human recombinant PDE4B2 (80 pM) is incubated for 2 hours with 3 nM cAMP in buffer containing 1×HBSS, 5 mM HEPES, 3 mM $MgCl_2$, 0.1% BSA, pH 7.4 with or without test compounds. The enzymatic reactions are efficiently stopped by the addition of 500 µM IBMX present in the combined Stop/Detection buffer containing europium (Eu) chelate-labeled cAMP tracer and cAMP-specific monoclonal antibodies (mAb) labelled with the ULight™ dye. Samples are then further incubated for 1 h before plates are read at ex 340 nm and em at 665 nm and 615 nm on an EnVision reader. $IC_{50}$ values are determined from competition curves using a non-linear curve fitting program.

PDE4 Cell Free Assay Protocol:

PDE4 activity is determined in U937 human monocytic supernatants cells lysate. Cells are cultured, harvested and supernatant fraction prepared essentially as described in Torphy T J et al., J. Pharmacol. Exp. Ther. 1992; 263:1195-1205, which is incorporated herein by reference in its entirety. U937 cells are grown at 37° C., 5% $CO_2$ in RPMI 1640 with GlutaMAX™-I medium supplemented with 10% fetal bovine serum and 100 µg/ml Pen-strep (Gibco). Cells are harvested and washed twice by centrifugation (150×g, 8 min) in cold PBS. Washed cells are re-suspended in cold Krebs-Ringer-Henseleit buffer at a final concentration $20 \times 10^6$ cells/ml and sonicated. After centrifugation at 15000×g for 20 minutes, the supernatants are pooled, divided in aliquots and stored at −80° C. PDE4 activity is determined in cells supernatants by assaying cAMP disappearance from the incubation mixtures.

The concentration of the test compounds ranges between $10^{-12}$ M and $10^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance ($IC_{50}$). Percentage of inhibition of PDE4 activity is calculated, assuming cAMP disappearance in the absence of inhibitors as 100% and cAMP disappearance in heat inactivated samples as 0%.

In Vitro Determination of M3 Antagonism:

In vitro determination of M3 antagonism for compounds of the invention may be determined according to one of the protocols herebelow reported:

M3 Receptor Radioligand Binding Assay:

Human $M_3$ receptor membranes (15 µg/well) from Perkin Elmer are incubated with 0.52 nM Scopolamine Methyl Chloride, [N-methyl-3H] with or without test compounds, or a saturating concentration of Atropine (5 µM) for the determination of non-specific binding. The assay is carried out in 96-well polypropylene plates in a volume of 250 µl. The assay buffer used is 50 mM Tris-HCl, 154 mM NaCl (pH 7.4). The final assay concentration of DMSO is 0.5% (v/v). The plates are sealed and incubated for 2 hours at room temperature on an orbital shaker (slow speed). Membranes are harvested onto 96-well unifilter GF/C filter plates pre-treated with 0.5% polyethyleneimine (v/v), using a filter manifold, washed four times with 200 µl of assay buffer. The plates are dried before addition of 50 µl of microscint-0, sealed then read in a Trilux Microbeta scintillation counter. $IC_{50}$ values are determined from competition curves using a non-linear curve fitting program. $K_i$ values are calculated from $IC_{50}$ values by the Cheng and Prusoff equation.

Representative compounds of the invention, when tested in one of the above reported protocols, displayed an $IC_{50}$ lower than 100 nM.

M3 Binding Assay:

CHO-K1 clone cells expressing the human M3-receptor (Swissprot P20309) were harvested in $Ca^{++}/Mg^{++}$ free phosphate-buffered saline and collected by centrifugation at 1500 rpm for 3 minutes. The pellets were resuspended in ice cold buffer A (15 mM Tris-HCl pH 7.4, 2 mM $MgCl_2$, 0.3 mM EDTA, 1 mM EGTA) and homogenized by a PBI politron (setting 5 for 15 s). The crude membrane fraction was collected by two consecutive centrifugation steps at 40000 g for 20 minutes at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non-selective muscarinic radioligand [$^3$H]-N-methyl scopolamine (see Mol. Pharmacol. 45:899-907, which is incorporated herein by reference in its entirety) was used to label the M3 binding sites. Binding experiments were performed in duplicate (ten point concentrations curves) in 96 well plates at radioligand concentration of 0.1-0.3 nM. The non-specific binding was determined in the presence of cold N-methyl scopolamine 10 µM. Samples (final volume 0.75 ml) were incubated at room temperature for 90 minutes. The reaction was terminated by rapid filtration through GF/B Unifilter plates and two washes (0.75 ml) with cold buffer C using a Packard Filtermate Harvester. Radioactivity on the filters was measured by a microplate scintillation counter TriCarb 2500 (PerkinElmer).

Representative compounds of the invention, when tested in one of the above reported protocols, displayed an $IC_{50}$ lower than 100 nM.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (I):

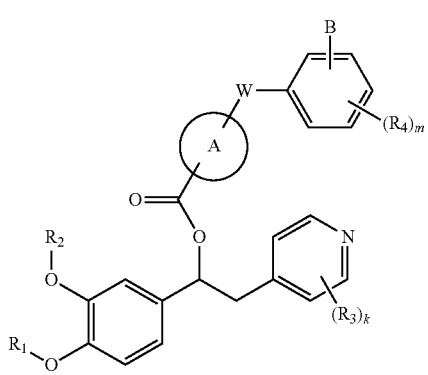

wherein:

$R_1$ and $R_2$ are different or the same and are:

H;

$(C_3-C_7)$ cycloalkylcarbonyl;

$(C_1-C_6)$ alkyl, optionally substituted by one or more substituents selected from the group consisting of $(C_3-C_7)$ cycloalkyl and $(C_5-C_7)$ cycloalkenyl;

$(C_1-C_6)$ haloalkyl;

$(C_3-C_7)$ cycloalkyl;

$(C_5-C_7)$ cycloalkenyl;

$(C_2-C_6)$ alkenyl; or $(C_2-C_6)$ alkynyl;

or $R_1$ and $R_2$, together with the interconnecting atoms, form a 2,2-difluoro-1,3-dioxolane ring represented by formula (r) fused to the phenyl moiety which bears groups —$OR_1$ and —$OR_2$, wherein asterisks indicate carbon atoms shared with the phenyl ring:

each $R_3$ is independently CN, $NO_2$, $CF_3$, or a halogen atom;

k is zero or an integer ranging from 1 to 3;

A is a saturated and monocyclic $(C_3-C_7)$ heterocycloalkylene group;

W is:

[1]-$(CH_2)_sC(O)$-[2] wherein s is zero or 1;

[1]-$C(O)(CH_2)_j$[2], wherein j is 1 or 2;

[1]-$SO_2(CH_2)_t$-[2] wherein t is zero, 1 or 2;

[1]-$(CH_2)_ySO_2$-[2] wherein y is 1 or 2;

[1]$(CH_2)_f$-[2] wherein f is 1 or 2; or

[1]$C(O)(CH_2)_2SO_2$-[2];

wherein [1] and [2] indicate the points of attachment for group W with, respectively, ring A and the phenyl moiety;

each $R_4$ is hydrogen, halogen, $(C_1-C_4)$ alkyl, $(C_1-C_4)$ alkoxy, $(C_1-C_4)$haloalkyl, hydroxy, —$SO_2NR_5R_6$, —CN, or —$NR_7SO_2R_8$, and wherein said $(C_1-C_4)$ alkyl and said $(C_1-C_4)$ alkoxy are optionally substituted by one $(C_3-C_7)$ cycloalkyl group, $R_5$ is hydrogen or $(C_1-C_6)$ alkyl;

$R_6$ is hydrogen or $(C_1-C_6)$ alkyl;

$R_7$ is hydrogen or $(C_1-C_6)$ alkyl;

$R_8$ is hydrogen or $(C_1-C_6)$ alkyl;

m is an integer ranging from 1 to 3;

B is selected from:

a group represented by formula (a) wherein the asterisk indicates the point of attachment for group B to the phenyl ring:

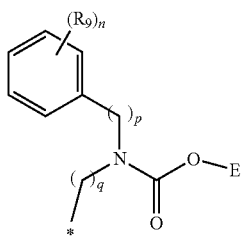

wherein
p is zero or 1;
q is zero or 1;
each $R_9$ is independently halogen, $(C_1-C_4)$ alkyl, $(C_1-C_4)$ alkoxy, $(C_1-C_4)$haloalkyl, hydroxy, $-SO_2NR_{10}R_{11}$, $-CN$, or $-NR_{12}SO_2R_{13}$, and wherein said $(C_1-C_4)$ alkyl and said $(C_1-C_4)$ alkoxy are optionally substituted by one $(C_3-C_7)$ cycloalkyl group,
$R_{10}$ is hydrogen or $(C_1-C_6)$ alkyl;
$R_{11}$ is hydrogen or $(C_1-C_6)$ alkyl;
$R_{12}$ is hydrogen or $(C_1-C_6)$ alkyl;
$R_{13}$ is hydrogen or $(C_1-C_6)$ alkyl;
n is an integer ranging from 1 to 3;
E is a nitrogen containing group which is:
  a group (c) which is $-(CH_2)_g-NR_{14}R_{15}$ wherein g is an integer ranging from 1 to 4 and $R_{14}$ and $R_{15}$ are independently hydrogen or $(C_1-C_4)$ alkyl; or
  a group (d) which is a saturated monocyclic or bicyclic or tricyclic heterocyclic ring system optionally substituted by one or two groups $R_{16}$ which are at each occurrence are independently $(C_1-C_4)$ alkyl or benzyl;
a group of formula (b) wherein the asterisk indicates the point of attachment for group B to the phenyl ring:

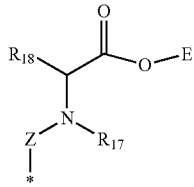

wherein
$R_{17}$ is hydrogen, $(C_1-C_4)$ alkyl, or $-SO_2(C_1-C_4)$alkyl;
$R_{18}$ is an aryl group or a 5 to 11 membered heteroaryl group, wherein said aryl group and said heteroaryl group are optionally substituted by 1 to 3 groups $R_{19}$;
$R_{19}$ is at each occurrence independently halogen, $(C_1-C_4)$haloalkyl, hydroxy, $-SO_2NR_{20}R_{21}$, $-CN$, $-NR_{22}SO_2R_{23}$, $(C_1-C_4)$ alkyl, or $(C_1-C_4)$ alkoxy wherein said $(C_1-C_4)$ alkyl and said $(C_1-C_4)$ alkoxy are optionally substituted by one $(C_3-C_7)$ cycloalkyl group, and wherein
$R_{20}$ is hydrogen or $(C_1-C_6)$ alkyl;
$R_{21}$ is hydrogen or $(C_1-C_6)$ alkyl;
$R_{22}$ is hydrogen or $(C_1-C_6)$ alkyl;
$R_{23}$ is hydrogen or $(C_1-C_6)$ alkyl;
Z is a bond or a divalent radical which is $-(CH_2)-$, $-(CH_2)_2-$, $-S-$, $-S(O)-$, $-S(O_2)-$, $-C(O)-$, or a group [5]$-(C_1-C_4)$alkylOC(O)-[6], wherein [5] and [6] represent, respectively the point of attachment of group Z to the phenyl ring and to the nitrogen atom; and
E is a group as above defined or an N-oxide on the pyridine ring, or a pharmaceutically acceptable salt thereof.

2. A compound, N-oxide, or pharmaceutically acceptable salt according to claim 1, which is represented by formula (IB):

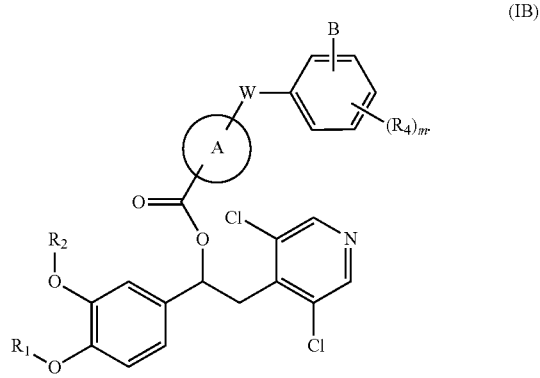

3. A compound, N-oxide, or pharmaceutically acceptable salt according to claim 1, which is represented by formula (IA):

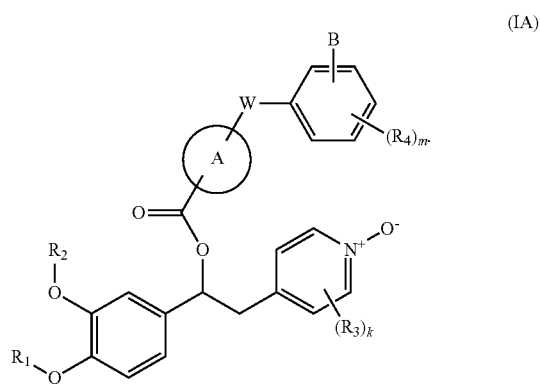

4. A compound, N-oxide, or pharmaceutically acceptable salt according to claim 1, which has the absolute configuration of carbon (1) shown in formula (I)':

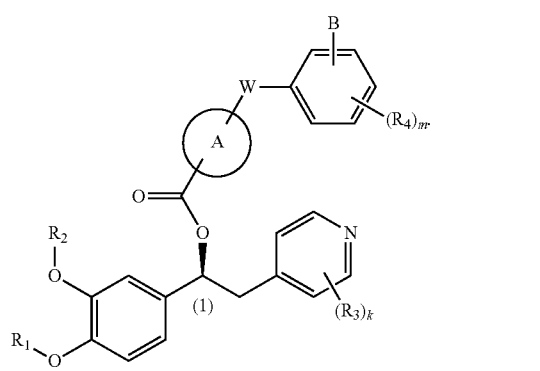

5. A compound, N-oxide, or pharmaceutically acceptable salt according to claim 1, wherein:

A is one of the divalent radicals shown below:

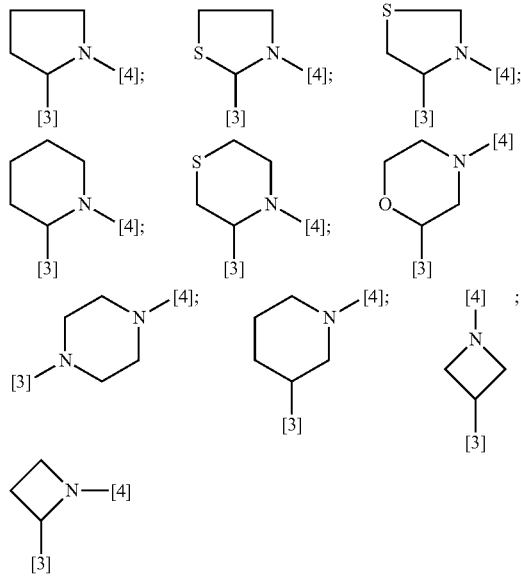

wherein the symbols [3] and [4] indicate the points of connection for group A with, respectively, the carbonyl group and W; and E is a group (d) represented by formula (i), (ii), (iii) or (iv):

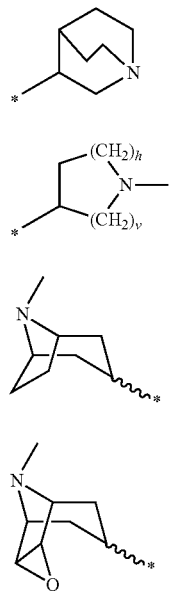

wherein:
h=1, 2 or 3;
v=1, 2 or 3.

6. A compound, N-oxide, or pharmaceutically acceptable salt according to claim 1, which is a compound selected from the group consisting of

[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[2-oxo-1-phenyl-2-[(3R)-quinuclidin-3-yl]oxy-ethyl]carbamoyl]phenyl]sulfonylthiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[(N-[(3R)-quinuclidin-3-yl]oxycarbonyl anilino)methyl]benzoyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[2-oxo-1-phenyl-2-[(3R)-quinuclidin-3-yl]oxy-ethyl]amino]phenyl]sulfonylpyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2R)-1-[3-[[1-(3-fluorophenyl)-2-oxo-2-[(3R)-quinuclidin-3-yl]oxy-ethyl]amino]phenyl]sulfonylpyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[2-oxo-1-phenyl-2-[(3R)-quinuclidin-3-yl]oxy-ethyl]amino]phenyl]sulfonylthiazolidine-2-carboxylate;

[(1S)-2-(3,5-dichloro-1-oxido-pyridin-1-ium-4-yl)-1-(3,4-dimethoxyphenyl)ethyl](2S)-3-[3-[[2-oxo-1-phenyl-2-[(3R)-quinuclidin-3-yl]oxy-ethyl]carbamoyl]phenyl]sulfonylthiazolidine-2-carboxylate;

[(1S)-2-(3,5-dichloro-1-oxido-pyridin-1-ium-4-yl)-1-(3,4-dimethoxyphenyl)ethyl](2S)-1-[3-[(2-fluoro-N-[(3R)-quinuclidin-3-yl]oxycarbonyl-anilino)methyl]benzoyl]piperidine-2-carboxylate;

[(1S)-2-(3,5-dichloro-1-oxido-pyridin-1-ium-4-yl)-1-(3,4-dimethoxyphenyl)ethyl](4R)-3-[3-[(2-fluoro-N-[(3R)-quinuclidin-3-yl]oxycarbonyl-anilino)methyl]benzoyl]thiazolidine-4-carboxylate;

[(1S)-2-(3,5-dichloro-1-oxido-pyridin-1-ium-4-yl)-1-(3,4-dimethoxyphenyl)ethyl](2S)-1-[3-[(2-fluoro-N-[(3R)-quinuclidin-3-yl]oxycarbonyl-anilino)methyl]benzoyl]pyrrolidine-2-carboxylate;

[(1S)-2-(3,5-dichloro-1-oxido-pyridin-1-ium-4-yl)-1-(3,4-dimethoxyphenyl)ethyl]1-[3-[(2-fluoro-N-[(3R)-quinuclidin-3-yl]oxycarbonyl-anilino)methyl]benzoyl]azetidine-3-carboxylate; and

[(1S)-2-(3,5-dichloro-1-oxido-pyridin-1-ium-4-yl)-1-(3,4-dimethoxyphenyl)ethyl](2S)-1-[4-[(2-fluoro-N-[(3R)-quinuclidin-3-yl]oxycarbonyl-anilino)methyl]phenyl]sulfonylpyrrolidine-2-carboxylate or a pharmaceutically acceptable salt of said compound.

7. A pharmaceutical composition, comprising a compound, N-oxide, or pharmaceutically acceptable salt according to claim 1 and at least one pharmaceutically acceptable carrier.

8. A pharmaceutical composition, according to claim 7, further comprising another active ingredient.

9. An inhalation device, comprising a pharmaceutical composition according to claim 7.

10. A kit, comprising a pharmaceutical composition according to claim 7 and a device which is a single- or multi-dose dry powder inhaler, a metered dose inhaler, or a nebulizer.

11. A pharmaceutical composition, comprising a compound, N-oxide, or pharmaceutically acceptable salt according to claim 2 and at least one pharmaceutically acceptable carrier.

12. A pharmaceutical composition, comprising a compound, N-oxide, or pharmaceutically acceptable salt according to claim 3 and at least one pharmaceutically acceptable carrier.

13. A pharmaceutical composition, comprising a compound, N-oxide, or pharmaceutically acceptable salt according to claim 4 and at least one pharmaceutically acceptable carrier.

14. A pharmaceutical composition, comprising a compound, N-oxide, or pharmaceutically acceptable salt according to claim 5 and at least one pharmaceutically acceptable carrier.

15. A pharmaceutical composition, comprising a compound, N-oxide, or pharmaceutically acceptable salt according to claim 6 and at least one pharmaceutically acceptable carrier.

16. A pharmaceutical composition, according to claim 8, wherein said another active ingredient is selected from the group consisting of a beta2-agonist, an antimuscarinic agent, a corticosteroid, a mitogen-activated protein kinase (P38 MAP kinase) inhibitor, a nuclear factor kappa-B kinase subunit beta (IKK2) inhibitor, a human neutrophil elastase (HNE) inhibitor, a phosphodiesterase 4 (PDE4) inhibitor, a leukotriene modulator, a non-steroidal anti-inflammatory agent (NSAID), a mucus regulator, and a combination thereof.

* * * * *